(12) United States Patent
Singh et al.

(10) Patent No.: US 7,456,296 B2
(45) Date of Patent: Nov. 25, 2008

(54) METHOD FOR PREPARATION OF CRYSTALLINE PERINDOPRIL ERBUMINE

(75) Inventors: Girij Pal Singh, Pune (IN); Himanshu Madhav Godbole, Pune (IN); Sagar Purushottam Nehate, Pune (IN)

(73) Assignee: Lupin Ltd, Mumbai (IN)

( * ) Notice: Subject to any disclaimer, the term of this patent is extended or adjusted under 35 U.S.C. 154(b) by 167 days.

(21) Appl. No.: 10/576,386

(22) PCT Filed: Oct. 21, 2003

(86) PCT No.: PCT/IN03/00340

§ 371 (c)(1),
(2), (4) Date: Apr. 19, 2006

(87) PCT Pub. No.: WO2005/037788

PCT Pub. Date: Apr. 28, 2005

(65) Prior Publication Data

US 2007/0149604 A1    Jun. 28, 2007

(51) Int. Cl.
*A61K 31/405* (2006.01)
*C07D 209/42* (2006.01)

(52) U.S. Cl. .................... 548/492; 514/419
(58) Field of Classification Search ............... 548/492; 514/419
See application file for complete search history.

(56) References Cited

U.S. PATENT DOCUMENTS 4,914,214 A    4/1990    Baliarda

FOREIGN PATENT DOCUMENTS

| EP | 1371659 | * 12/2003 |
| WO | WO 01/83439 | 11/2001 |
| WO | WO 01/87835 | 11/2001 |
| WO | WO 01/87836 | 11/2001 |

OTHER PUBLICATIONS

Guillory, "Generation of Polyjorphs, Hydrates, Solvates, and Amorphous Solids" in Polymorphism in Pharmaceutical Solids, vol. 95, Marcel Dekker, Inc., p. 183-226.* http://www.m-w.com/dictionary.*
http://www.dictionary.reference.com/browse/gradually.*

* cited by examiner

*Primary Examiner*—Kamal Saeed
*Assistant Examiner*—Sun Jae Y Loewe
(74) *Attorney, Agent, or Firm*—Volpe and Koenig, P.C.

(57) ABSTRACT

A process for preparation of crystalline perindopril erbumine of formula (II)

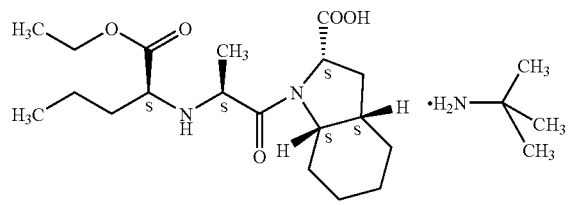

(II)

Figure 2:
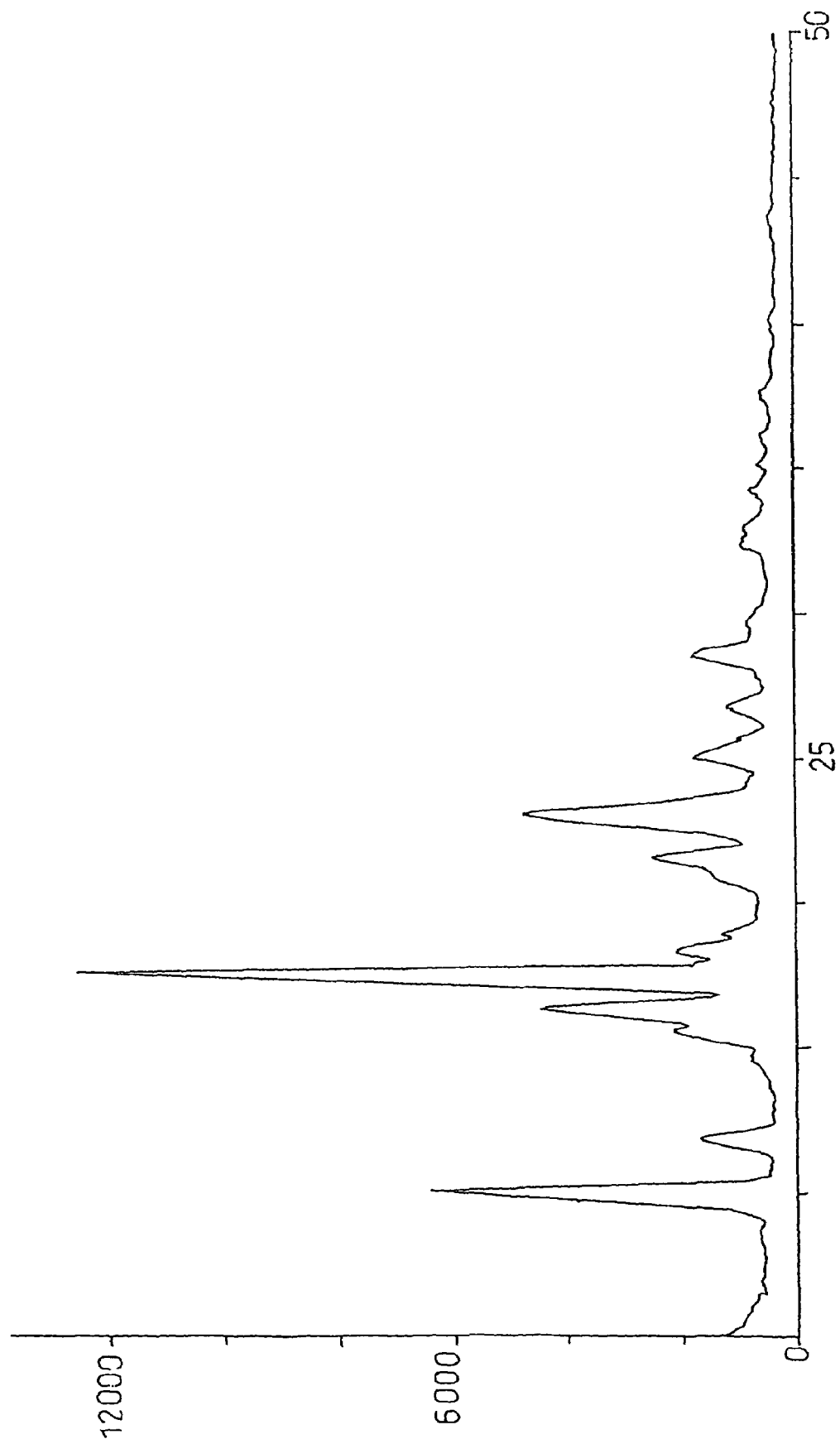

which exhibits the X-ray (powder) diffraction pattern like that shown in FIG. 2

The process comprises reacting a solution of perindopril of formula (I),

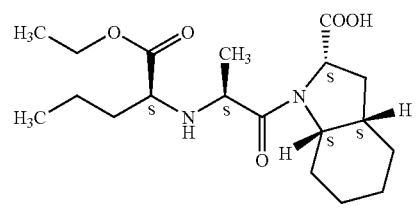

(I)

in a solvent selected from N,N-dimethylformamide, dimethyl acetals of lower aliphatic aldehydes, dimethyl ketals of lower aliphatic ketones and 1,2-dialkoxyethane with tertiary butylamine and crystallization of the erbumine salt thus obtained by heating the reaction mixture to reflux, filtering hot, cooling gradually to 20° C. to 30° C., and further cooling to 0° C. to 15° C. for 30 minutes to 1 hour and finally filtering off and drying the crystals.

1 Claim, 7 Drawing Sheets

METHOD FOR PREPARATION OF CRYSTALLINE PERINDOPRIL ERBUMINE

FIELD OF THE INVENTION

The present invention relates to a novel process for preparation of crystalline perindopril erbumine of formula (II)

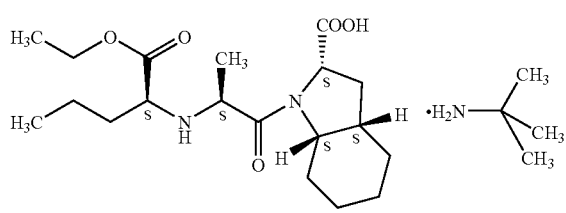

(II)

BACKGROUND OF THE INVENTION

The chemical entity (2S)-2-[(1S)-1-carbethoxybutylamino]-1-oxopropyl-(2S,3aS,7aS)-perhydroindole-2-carboxylic acid of formula (I), known generically as perindopril

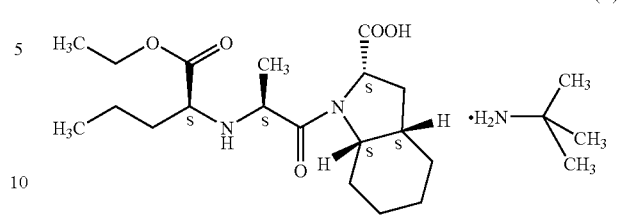

(II)

and its pharmaceutically acceptable salts, specially salt of perindopril with tertiary butyl amine i. e. perindopril erbumine of formula (II)

are therapeutically valuable ACE Inhibitors, useful for the treatment of hypertension.

The drug is commercially sold: as the erbumine salt and was approved in the USA on Dec. 30, 1993 for the treatment of hypertension. The final printed label of the approved drug, ACEON® Tablets states that perindopril erbumine is a white, crystalline powder with a molecular weight of 368.47 (free acid) or 441.61 (salt form) and freely soluble in water (60% w/w), alcohol and chloroform.

Several methods are known for preparation of perindopril and perindopril erbumine as well as methods for preparation of compounds useful as intermediates for preparation of perindopril and perindopril erbumine. A brief summary of such methods are given hereinbelow:

U.S. Pat. No. 4,508,729, which is the product patent of perindopril, discloses a method for preparation of perindopril monoammonium salt, as a mixture of two diastereomers, involving reductive amination of (2S)-1-[(S)-alanyl]-2-carboxyperhydroindole with pyruvic acid in the presence of sodium cyanoborohydride. The (2S)-1-[(S)-alanyl]-2-carboxyperhydroindole, in turn is prepared by reaction of (2S)-2-ethoxycarbonylperhydroindole with L-BOC.-alanine to give (2S)-N-[(S)-BOC.-alanyl]-2-ethoxycarbonylperhydroindole, which on step-wise removal of the carboxyl and amino protecting groups gives (2S)-1-[(S)-alanyl]-2-carboxyperhydroindole. The synthesis is schematically represented hereinbelow.

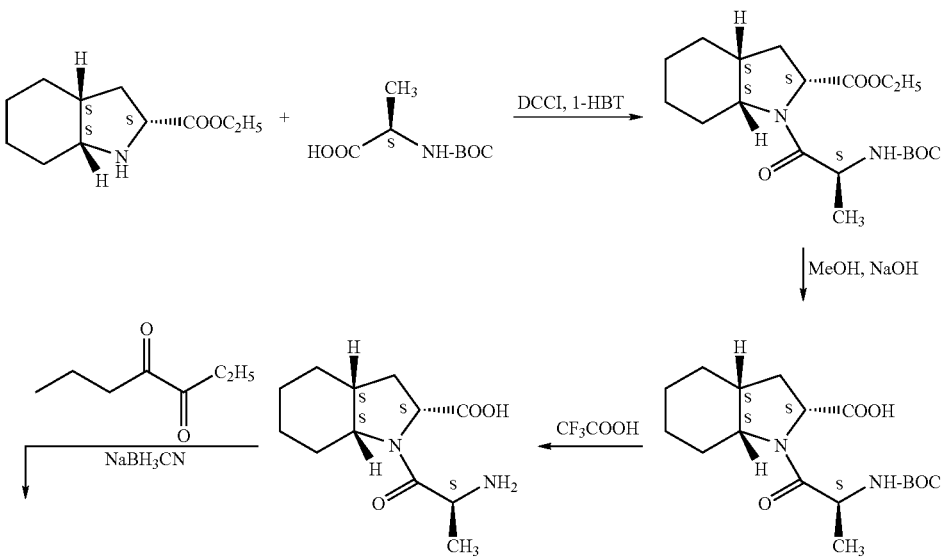

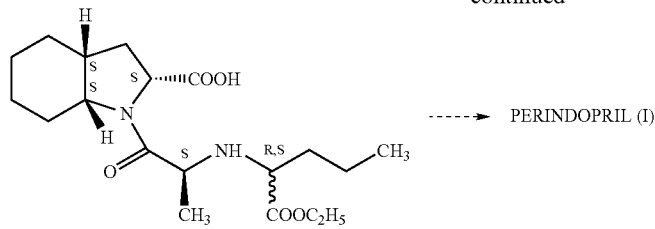

→ PERINDOPRIL (I)

However, this method gives perindopril as a mixture of two diastereomers, of which only one is a therapeutic. Further, there is neither any enabling disclosure in the patent as to how the diastereomers are separated to give perindopril, having the desired (S) configuration for all the five chiral centers in the molecule nor any method is disclosed as to how the tert-butylamine salt i. e. perindopril erbumine can be prepared.

Moreover, the method involves protection of the amino group of the alanine moiety as the t-BOC group, which necessitates use of corrosive trifluoroacetic acid for its subsequent removal, thereby rendering the method industrially unattractive.

U.S. Pat. No. 4,902,817 discloses a stereoselective process for the industrial synthesis of N-[(S)-1-carbethoxybutyl]-(S)-alanine comprising reaction of ethyl-L-norvalinate hydrochloride with pyruvic acid under catalytic hydrogenation conditions. The N-[(S)-1-carbethoxybutyl]-(S)-alanine thus obtained is a key intermediate for perindopril. The synthesis is schematically represented hereinbelow.

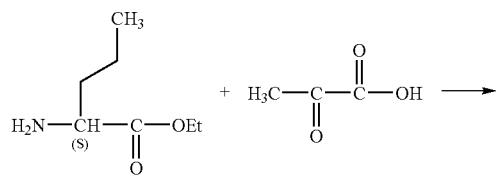

-continued

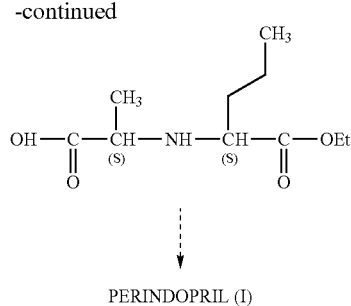

↓

PERINDOPRIL (I)

However, this patent does not provide any enabling method for preparation of perindopril or perindopril erbumine from N-[(S)-1-carbethoxybutyl]-(S)-alanine thus obtained.

EP 0 309 324 discloses another method for synthesis of (S,S) diastereoisomer of N-[(S)-1-carbethoxybutyl]-(S)-alanine, a key intermediate for perindopril comprising reaction of L-alanine benzyl ester p-toluenesulfonate with ammonia to form the free base, which is condensed with ethyl α-bromo valerate to give a racemic mixture of N-[(S)-1-carbethoxybutyl]-(S)-alanine and N-[(R)-1-carbethoxybutyl]-(S)-alanine. The (S) isomer is separated by resolution with maleic acid and subsequent removal of the benzyl ester group provides the (S,S) diastereoisomer of N-[(S)-1-carbethoxybutyl]-(S)-alanine, which can be further elaborated to perindopril and perindopril erbumine.

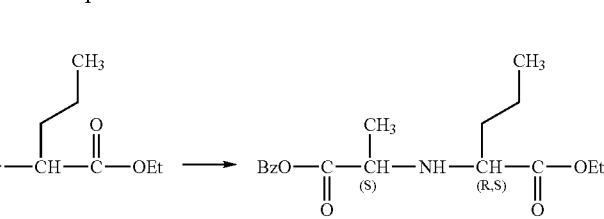

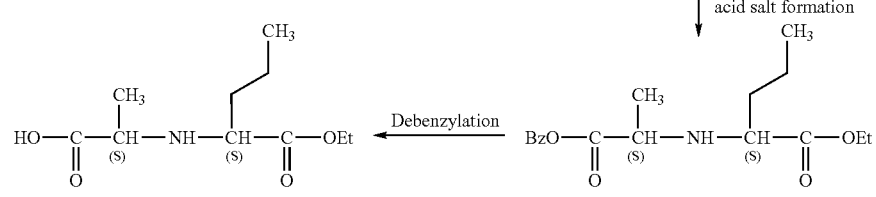

↓

PERINDOPRIL (I)

However, this patent, also does not provide any enabling method for preparation of perindopril or perindopril erbumine from N-[(S)-1-carbethoxybutyl]-(S)-alanine thus obtained.

WO 01/56353 discloses yet another method for preparation of the (S,S) diastereoisomer of N-[(S)-1-carbethoxybutyl]-(S)-alanine, a key intermediate for perindopril comprising reacting sodium pyruvate with L-norvaline ester under reducing conditions using palladium carbon as catalyst.

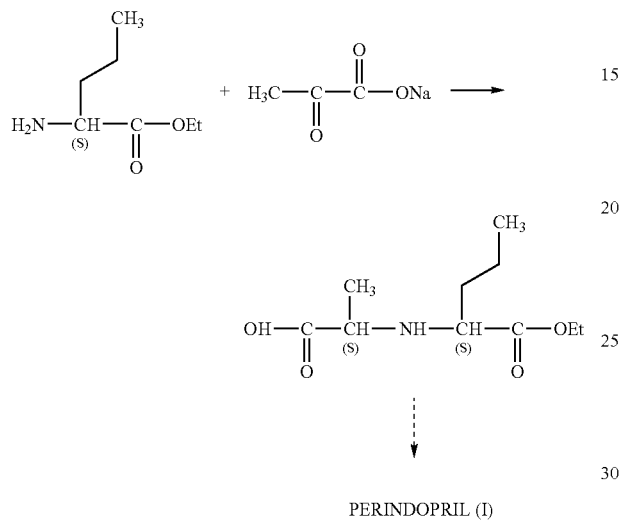

PERINDOPRIL (I)

However, this patent, also does not provide any enabling method for preparation of perindopril or perindopril erbumine from N-[(S)-1-carbethoxybutyl]-(S)-alanine thus obtained.

WO 01/56972 discloses a further method for preparation of the (S,S) diastereoisomer of N-[(S)-1-carbethoxybutyl]-(S)-alanine, a key intermediate for perindopril comprising reacting 1-alanine and ethyl 2-oxo-pentanoic acid under catalytic hydrogenation conditions and isolating the product at a pH between 3 to 3.5, followed by crystallization.

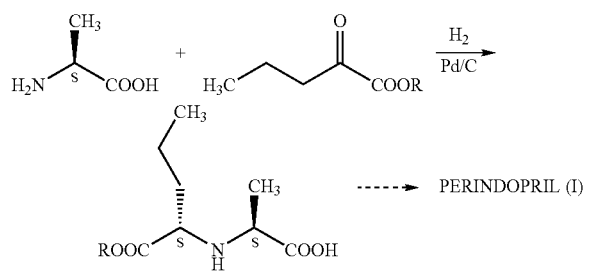

However, this patent, also does not provide any enabling method for preparation of perindopril or perindopril erbumine from N-[(S)-1-carbethoxybutyl]-(S)-alanine thus obtained.

EP 1 256 590 discloses a process for preparation of (2S, 3aS, 7aS)-1-(S)-alanyl-octahydro-1H-indole-2-carboxylic acid, an intermediate for perindopril comprising reaction of (2S)-2,3-dihydroindole-2-carboxylic acid with t-BOC-L-alanine to form the amide compound followed by hydrogenation to give (2S, 3aS, 7aS)-1-(S)-alanyl-octahydro-1H-indole-2-carboxylic acid, which can be further elaborated to perindopril.

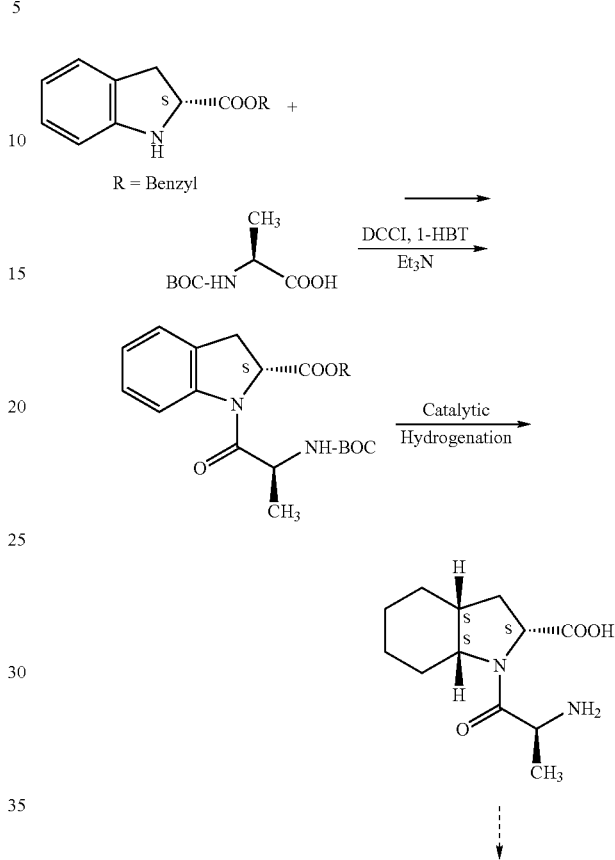

PERINDOPRIL (I)

However, this patent does not provide any enabling method for preparation of perindopril or perindopril erbumine from (2S, 3aS, 7aS)-1-(S)-alanyl-octahydro-1H-indole-2-carboxylic acid thus obtained.

WO 96/33984 discloses N-sulfoxy anhydrides of N-[1-(S)-ethoxycarbonyl-3-phenylpropyl/butyl-S-alanine, and a process for preparation of several ACE inhibitors including perindopril using the said N-sulfoxy anhydride compounds. The N-sulfoxy anhydride is in turn prepared by reacting the corresponding carboxylic acid compound with N-(chlorosulfinyl)-heterocyclic compound, wherein the heterocycle is an alkyl imidazole, benzimidazole, tetrazole or other similar heterocyclic compounds.

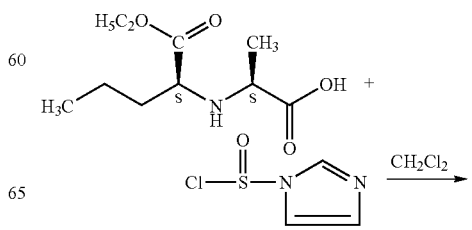

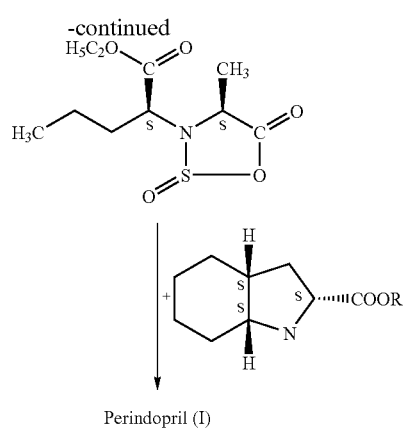

Perindopril (I)

However, this patent application specifically discloses detailed methods for synthesis of trandolapril, but not perindopril.

GB 2 095 252 claims certain N-(substituted aminoalkanoyl) heterocyclic compounds having antihypertensive and ACE Inhibition activity and a process for preparation thereof, which comprises an amide forming reaction of a suitable amine compound and the reactive derivatives of the suitable carboxylic acid compound. The reactive carboxylic derivatives mentioned therein include acyl halides, anhydrides, mixed anhydrides, lower alkyl esters, carbodiimides, carbonyl diimidazoles and the like.

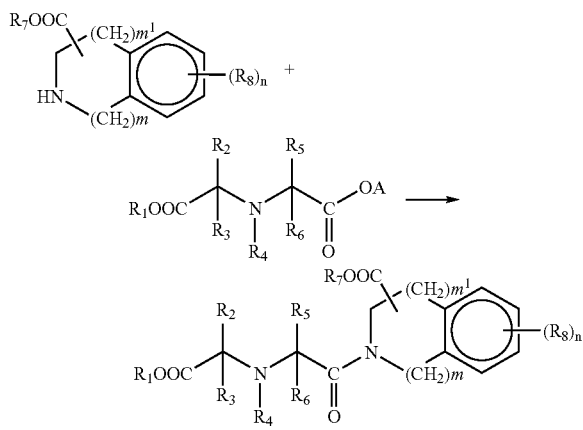

$R_1$, $R_7$ = H, Lower alkyl, or phenyl lower alkyl
$R_2$, $R_3$, $R_4$, $R_5$, and $R_6$ = H, alkyl, alkenyl, alkynyl, fused aryl-cycloakyl, aralkyl, cycloalkyl and heterocyclic
$m$ = integer from 0 to 2
$m^1$ = integer of 1 or 2
$n$ = integer of 0 to 4

However, this patent disclosure does not include perindopril as the antihypertensive and ACE inhibitory compounds mentioned therein.

DE. 197 21 290 describes a method for preparation of several ACE Inhibitors of formula (D), including perindopril, wherein Z is alkyl or phenyl and $R_1$ is an amino acid as found in commercially valuable ACE inhibitors. The process comprises the steps of first silylating the compound of formula (A) to give the (bis)silyl derivative of formula (B), followed by reaction of compound (B) with thionyl chloride to give the silylated acid chloride derivative of formula (C). Compound (C) is then reacted with the respective amino acid, $R_1$H to give compound of formula (D).

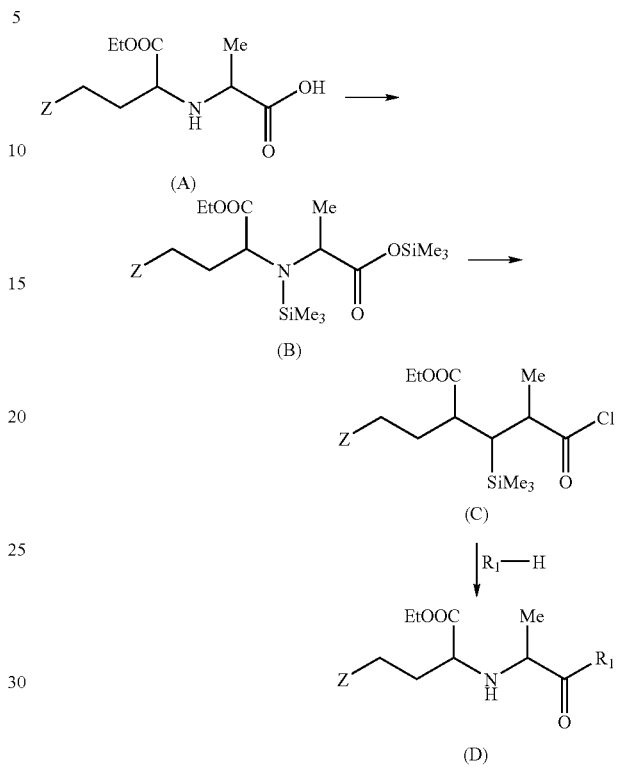

This method is however, lengthy and not cost-effective since there is a step of silylation using expensive silylating agents and subsequent step of desilylation involved.

The first enabling industrial method for preparation of perindopril erbumine was disclosed. in U.S. Pat. No. 4,914,214 comprising reaction of (2S, 3aS,7aS)-2-carboxyperhydroindole, wherein the carboxylic acid at 2-position of the octahydroindole ring is protected as the benzyl group or is esterified with a linear or branched alkyl group, with (S,S) diastereoisomer of N-[(S)-1-carbethoxybutyl]-(S)-alanine in an alkaline medium in the presence of a catalyst, such as dicyclohexylcarbodiimide and in the presence of 1-hydroxybenzotriazole to give perindopril benzyl or alkyl ester. Subsequent deprotection of the carboxylic acid protective group gives perindopril in the form of a base.

The perindopril free base is dissolved in a solvent chosen from lower aliphatic alcohol, acetonitrile, ethyl acetate or dioxane or mixtures thereof and the solution reacted with tert-butylamine to form perindopril erbumine, which is crystallized by heating the reaction mixture, filtering hot, cooling and finally filtering of the crystallized perindopril erbumine.

This patent gives a detailed description of synthesis of perindopril erbumine divided in three stages—one related to synthesis of (2S,3aS,7aS)-2-Carboxyoctahydroindole; second describing synthesis of N-[(S)-1-Carbethoxybutyl]-(S)-alanine and the third stage comprising reaction of the compounds obtained by stages one and two to give perindopril and perindopril erbumine thereof. The chemistry practiced therein is summarized in Scheme-I.

Scheme-I: Synthesis of Perindopril Erbumine as described in U.S. Pat. No. 4,914,214

Stage-I: Synthesis of (2S, 3aS, 7aS)-2-Carboxyoctahydroindole ester (A)

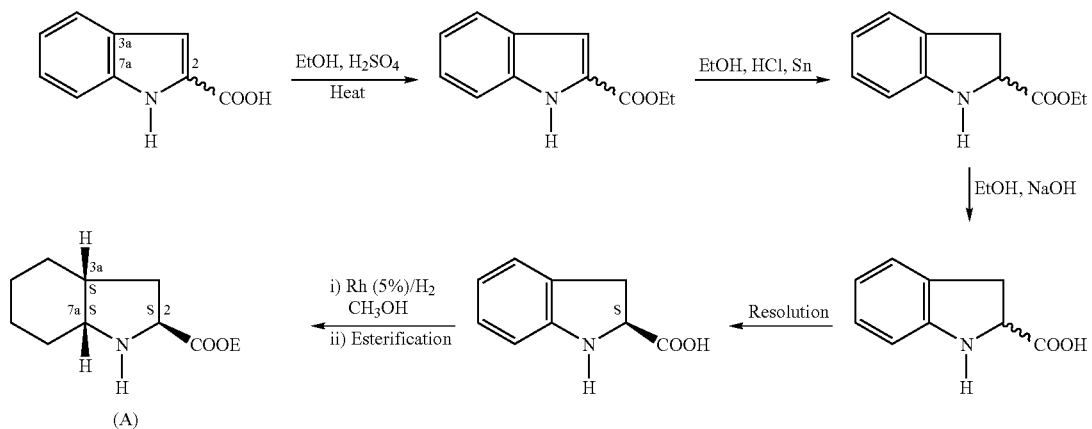

E = lower branched or linear alkyl or benzyl

Stage-II: Synthesis of N-[(S)-Carbethoxybutyl}-(S)-alanine (B)

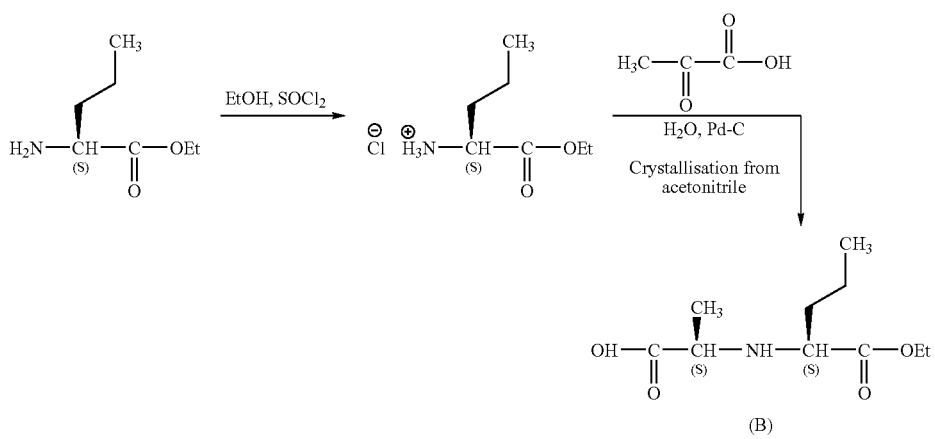

Stage-III: Preparation of Perindopril Erbumine (II)

i) t-BuNH²
   EtOAo, Lower alcohol,
   CH₃CN, or Dioxane
ii) Crystallisation from
    any of the above
    solvents or mixtures
    thereof

PERINDOPRIL
ERBUMINE (II)

However, apart from the description of synthesis given therein the U.S. Pat. No. 4,914,214 does not provide any detail of the crystal nature of perindopril erbumine obtained.

In addition, the method utilizes solvents such as acetonitrile and 1,4-dioxane for crystallization/purification of the erbumine salt, which come under the category of Class II solvents as categorized by International Conference of Harmonisation (ICH). The guidelines recommend that such solvents i. e. belonging to Class II category should not be used or their use should be limited in a method for manufacture of a drug substance.

WO 01/58868 discloses a method for preparation of perindopril erbumine comprising reacting benzyl ester of (2S, 3aS,7aS)-2-carboxyperhydroindole, p-toluenesulfonate salt with (S,S) diastereoisomer of N-[(S)-1-carbethoxybutyl]-(S)-alanine in the presence of 0.4 to 0.6 moles of 1-hydroxybenzotriazole; 1 to 1.2 moles of dicyclohexylcarbodiimide and 1 mole of triethylamine at 77° C. to give the dipeptide compound, which on debenzylation gives perindopril.

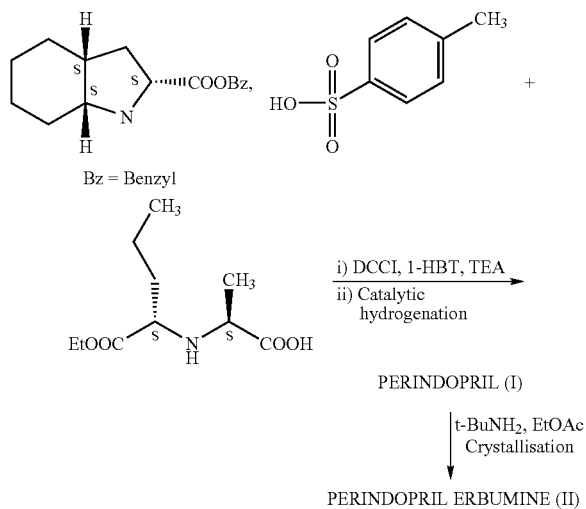

Example-3 of this patent application, describes a method for preparation of perindopril erbumine consisting refluxing a suspension of perindopril and tert-butylamine in ethyl acetate, followed by cooling the solution to 15-20° C. and isolating the crystallized product by filtration.

However, this application also does not provide any detail of the crystal nature of perindopril erbumine thus obtained.

EP 1 279 665 discloses N-carboxy anhydride of N-[1-(S)-ethoxycarbonyl-3-butyl-S-alanine (B), and a process for its preparation by reaction of N-[1-(S)-ethoxycarbonyl-3-butyl-S-alanine (A) with phosgene. The application further relates to a method for preparation of perindopril and perindopril erbumine using the said N-carboxy anhydride compound (B).

Claim 9 of this application recites a process for preparation of N-[1-(S)-ethoxycarbonyl-3-butyl-S-alanine (A), comprising reaction of a suitably protected alanine of formula (C) with a suitably functionalised pentanoic acid ester, in particular wherein the leaving group is a trifluromethanesulfonyloxy (—OSO$_2$CF$_3$) group of formula (D) as summarized in Scheme-II.

It might be mentioned herein that the chemistry embodied in claim 9 of EP 1 279 665 is obvious and anticipated from similar chemistry reported by D. W. Payling et. al. in *J. Med. Chem.*, 1991, 34, 430-447

Example-2 of this patent application, describes a method for preparation of perindopril erbumine consisting heating a mixture of perindopril and tert-butylamine in acetonitrile at 40° C., followed by cooling the solution to 5° C. and isolating the crystallized product by filtration. However, for reasons mentioned hereinearlier use of acetonitrile poses hazards in operability on a commercial scale.

Further, this application also does not provide any detail of the crystal nature of perindopril erbumine obtained.

Moreover, this method utilizes toxic and hazardous phosgene for preparation of the N-carboxy anhydride compound, thereby rendering it commercially unattractive.

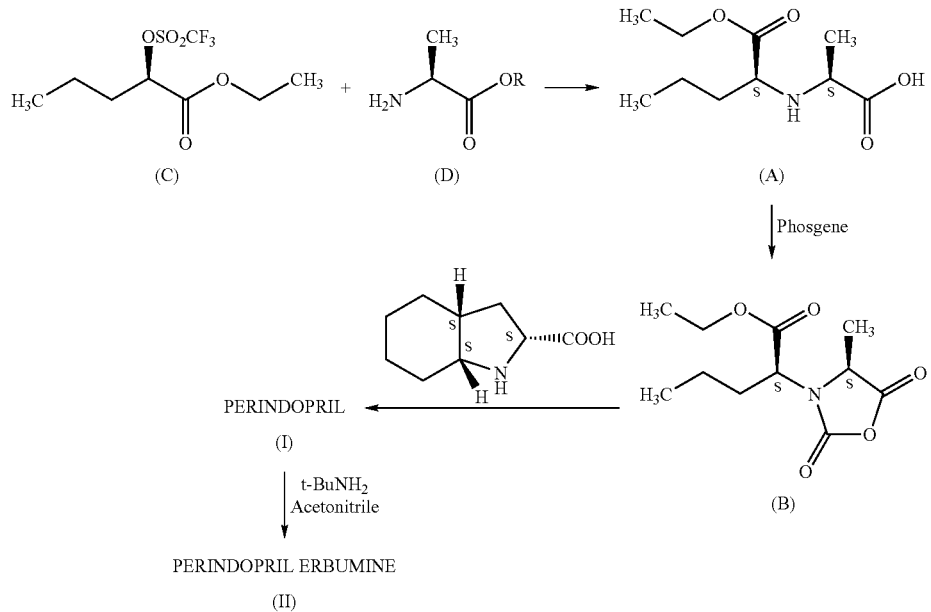

WO 01/87835, WO 01/87836 and WO 01/83439, all having an international filing date of Jul. 6, 2001 and drawing priority from three French Applications, all in turn having a filing date of Jul. 6, 2000 claim three different crystalline forms of perindopril erbumine and a process for preparation thereof.

WO 01/87835 teaches a crystalline form, designated as the α crystalline form of perindopril erbumine, which is obtained by bringing to reflux a solution of the erbumine salt of perindopril in ethyl acetate and cooling the solution progressively or gradually till complete crystallization.

WO 01/87836 teaches a crystalline form, designated as the β crystalline form of perindopril erbumine, which is obtained by bringing to reflux a solution of the erbumine salt of perindopril in dichloromethane and cooling the solution rapidly to 0° C. and isolation of the solid obtained by filtration. Alternatively, the β crystalline form is prepared by bringing to reflux a solution of the erbumine salt of perindopril in ethyl acetate and cooling the solution rapidly to 5° C. and isolation of the solid obtained by filtration.

WO 01/83439 teaches a crystalline form, designated as the γ crystalline form of perindopril erbumine, which is obtained by bringing to reflux a solution of the erbumine salt of perindopril in chloroform and cooling the solution rapidly to 0° C. and isolation of the solid obtained by filtration. Alternatively, the γ crystalline form is prepared by bringing to reflux a solution of the erbumine salt of perindopril in ethyl acetate and cooling the solution rapidly to 5° C. and isolation of the solid obtained by filtration, followed by suspending the solid in chloroform and agitating at room temperature for 5 to 10 days, and collecting the solid by filtration.

From the foregoing, it would be apparent that:
i) Neither the product patent of perindopril i. e. U.S. Pat. No. 4,508,729 nor the majority of the large number of subsisting process patents, contain any enabling disclosure for preparation of perindopril and/or perindopril erbumine,
ii) Those patents, in particular U.S. Pat. No. 4,914,214, WO 01/58868 and EP. 1 279 665 that do disclose a method for preparation of perindopril and perindopril erbumine, however, do not specify the crystal nature of the product thus obtained,
iii) The only report wherein the crystalline nature of perindopril erbumine has been specified are contained in. WO 01/87835, WO 01/87836 and WO 01/83439, covering three distinct crystalline forms, designated as α, β, or γ forms respectively and a process for preparation thereof, Thus, a need exists for a method of obtaining perindopril erbumine in a crystalline form conforming to that presumably existing in the marketed dosage form of ACEON® Tablets in a reproducible manner, which moreover, is obtained through utilization of solvents that are not frowned upon by regulatory authorities all over the world.

OBJECT OF THE INVENTION

It is thus the basic object of the present invention to provide a method for production of a crystalline form of perindopril erbumine conforming to that presumably existing in the marketed dosage form of ACEON® Tablets in a highly reproducible manner on an industrial scale, which moreover is easily amenable for formulation into a dosage form and possesses sufficient stability on storage and better physical characteristics like particle size, flowability or Compressibility Index which results in improved bioavailability.

Figure 6:
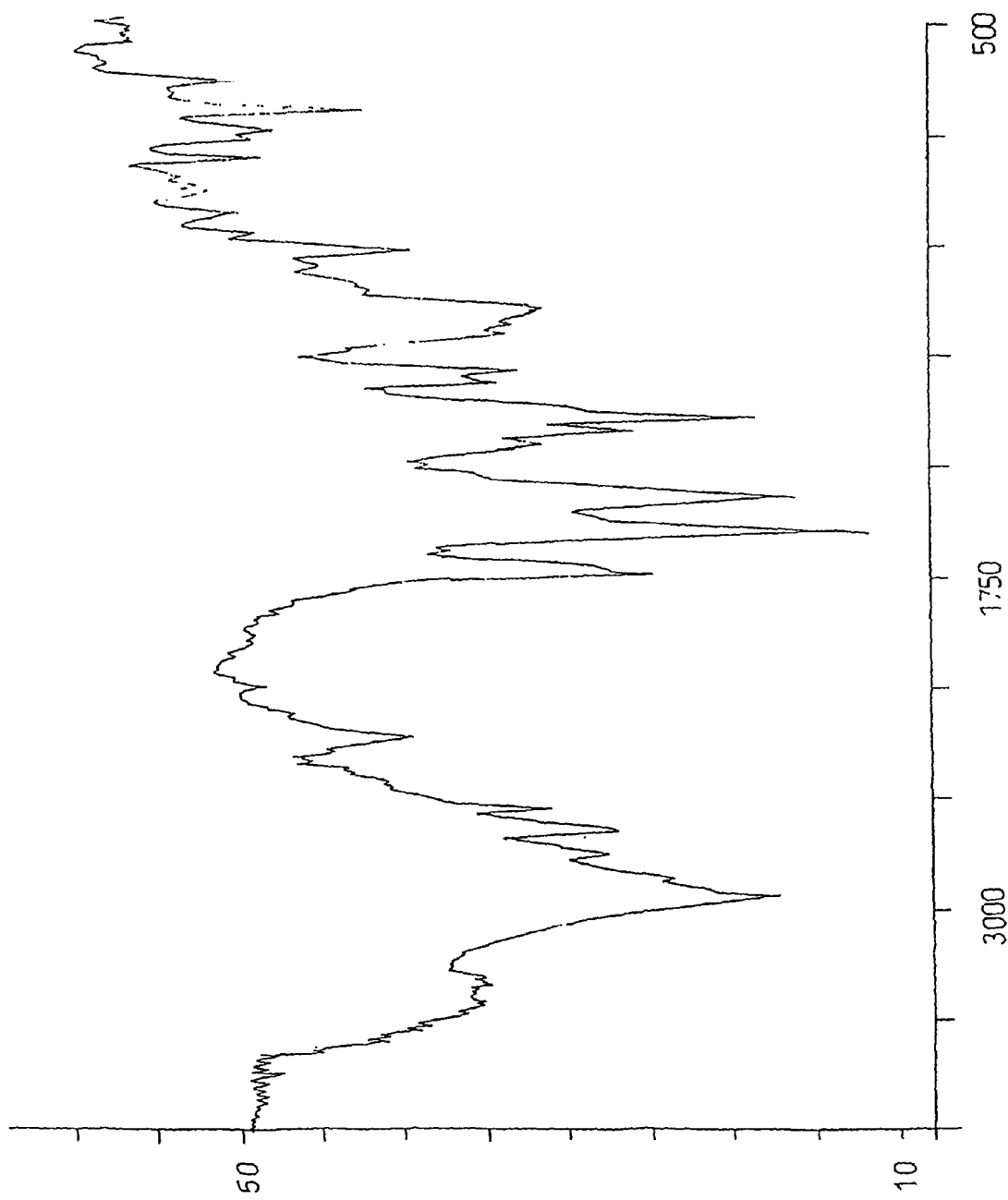

In accordance with the abovementioned objective, the present inventors first carried out the following studies, primarily to determine the crystal nature of perindopril erbumine prepared as per the methods disclosed in the prior art documents cited hereinbefore. This consisted synthesis and crystallization of perindopril erbumine from various sets of solvents exactly as per the methods disclosed in the prior art documents. The experiments carried out were:
a) Preparation of perindopril (I) exactly as per the method described in the Example Stage 1a to 3C, columns 6-9 of U.S. Pat. No. 4,914,214; converting the perindopril thus obtained to perindopril erbumine (II) and its crystallization from ethyl acetate exactly as per the method described in the Example Stage 3D, column 9 of U.S. Pat. No. 4,914, 214, the chemistry of which is summarized in Scheme-I and recording the DSC thermogram, IR spectrum, and X-ray (powder) diffraction pattern of the product thus obtained, the latter two being reproduced in Table-I and FIG. 6, given in a later part of this application,
b) Reproduction of the method given in section (a) hereinabove, but with substitution of ethyl acetate with 1,4-dioxane—a solvent claimed in U.S. Pat. No. 4,914,214 and recording the X-ray (powder) diffraction pattern of the product thus obtained, which in turn is reproduced in Table-II, given in a later part of this application,
c) Reproduction of the method given in section (a) hereinabove, but with substitution of ethyl acetate with acetonitrile—a solvent claimed in U.S. Pat. No. 4,914,214 and recording the X-ray (powder) diffraction pattern of the product thus obtained, which in turn is reproduced in Table-III, given in a later part of this application,
d) Reproduction of the method given in section. (a) hereinabove, but with substitution of ethyl acetate with a lower aliphatic alcohol, viz. methanol, ethanol, n-propanol etc. i. e. the solvents claimed in U.S. Pat. No. 4,914,214. In this case, however, no product crystallized out from any of these solvents even after standing in solution for several days.

The X-ray (powder) diffraction patterns of perindopril erbumine prepared and crystallized by the four different methods mentioned hereinabove revealed that the powder pattern of:
i) those prepared as per methods (e), (f) and (g) conformed with/were identical to that of the α, β, and γ crystalline forms respectively disclosed in. WO 01/87835, WO 01/87836 and WO 01/83439,
ii) that prepared as per method (a) i.e. crystallization from ethyl acetate as per the method described in U.S. Pat. No. 4,914,214 was different from any of the α, β, and γ crystalline forms reported in. WO 01/87835, WO 01/87836 and WO 01/83439.
iii) that prepared as per method (b) i.e. crystallization from 1,4-dioxane as per the method described in U.S. Pat. No. 4,914,214 was also different from any of the α, β, and γ crystalline forms reported in. WO 01/87835, WO 01/87836 and WO 01/83439, and also different from the crystalline form obtained through method (a), but identical with that obtained through method (c), and
iv) that prepared as per method (c) i.e. crystallization from acetonitrile as per the method described in U.S. Pat. No. 4,914,214 was different from any of the α, β, and γ crystalline forms reported in. WO 01/87835, WO 01/87836 and WO 01/83439, and also different from the crystalline form obtained through method (a), but identical with that obtained through method (b).

The above results clearly indicate that perindopril erbumine as crystallized from ethyl acetate as per the method described in Example Stage 3D, column 9 of U.S. Pat. No. 4,914,214 has the X-ray (powder) diffraction pattern summarized in Table-I and FIG. 1, whereas the nature of the crystals obtained on crystallization from acetonitrile and/or 1,4-dioxane are different from that obtained through use of ethyl acetate. Moreover, no product crystallized from a lower aliphatic alcohol, contrary to the claims of U.S. Pat. No. 4,914, 214.

The applicants have now found that a crystalline form of perindopril erbumine having identical and/or superimposable IR spectrum, DSC thermogram and X-ray (powder) diffraction pattern to that obtained on crystallization of perindopril erbumine from ethyl acetate as per the method described in Example Stage 3D, column 9 of U.S. Pat. No. 4,914,214—which presumably is the form found in the marketed samples of ACEON® Tablets of the drug—could be further obtained through a selection of solvents in a highly reproducible manner.

Various solvents, a list of which is given hereinbelow were tried for crystallization of perindopril erbumine, manufactured by any of the prior art methods or through methods invented by the inventors. These solvents are:
a) Ethers, both cyclic and acyclic, such as tetrahydrofuran, diethyl ether, diisopropyl ether etc.;
b) Ketonic solvents, both cyclic and acyclic, such as acetone, methyl ethyl ketone, methyl isobutyl ketone, 2-pentanone, cyclopentanone, cyclopentanone etc.;
c) Hydrocarbons, both aliphatic and aromatic, such as n-hexane, n-heptane, toluene, chlorobenzene etc;
d) Nitroalkanes, such as nitromethane, nitroethane, nitropropane etc.

The applicants have found that solvents selected from N,N-dimethylformamide, dimethyl acetals of lower aliphatic aldehydes, dimethyl ketals of lower aliphatic ketones and 1,2-dialkoxyethane give exclusively the crystalline form of perindopril erbumine having identical and/or superimposable JR spectrum, DSC thermogram and X-ray (powder) diffraction pattern to that obtained on crystallization of perindopril erbumine from ethyl acetate as per the method described in Example Stage 3D, column 9 of U.S. Pat. No. 4,914,214.

These solvents, unlike those used in the prior art, such as acetonitrile, 1,4-dioxane, dichloromethane, chloroform etc. are tolerated better by International Conference on Harmonization (ICH), and thereby rendering the process more amenable for commercial manufacture from a safety, environmental and regulatory point of view.

Further, the crystalline material obtained from crystallization of perindopril erbumine from these solvents was found to possess better physical characteristics like particle size, flowability or Compressability Index etc. compared to the material obtained by crystallization from ethyl acetate. These characteristics result in improved dissolution profile, which in turn, results in improved bioavailability, thereby rendering the crystalline perindopril erbumine obtained by the process of the present invention more amenable for formulation into a suitable dosage form.

SUMMARY OF THE INVENTION

Thus, in accordance with an aspect of the present invention there is provided a selective method for production of crystalline perindopril erbumine of formula (II), possessing the X-ray (powder) diffraction pattern, which moreover, is easily amenable for formulation into a dosage form and possesses sufficient stability on storage,

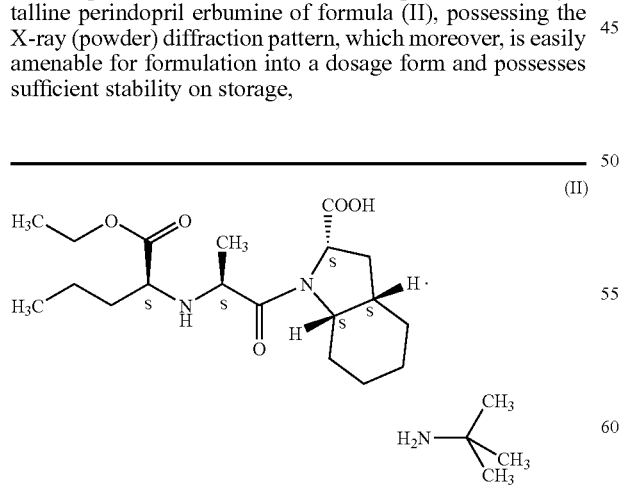

| d-spacing (Å) | Angle (°2θ) | Relative Intensity (%) |
|---|---|---|
| 10.239 | 8.628 | 1.16 |
| 8.886 | 9.945 | 49.45 |

-continued

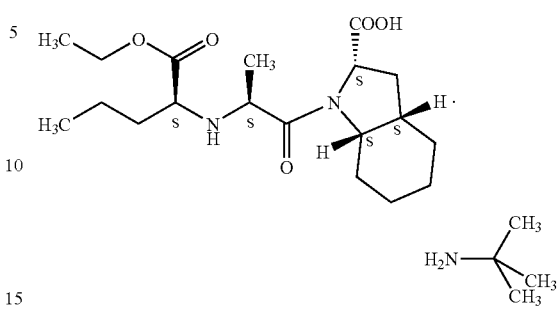

| d-spacing (Å) | Angle (°2θ) | Relative Intensity (%) |
|---|---|---|
| 7.453 | 11.863 | 10.26 |
| 6.054 | 14.618 | 3.35 |
| 5.716 | 15.487 | 14.10 |
| 5.435 | 16.294 | 33.06 |
| 5.082 | 17.434 | 100.00 |
| 4.844 | 18.296 | 14.06 |
| 4.661 | 19.023 | 5.88 |
| 4.278 | 20.744 | 8.50 |
| 4.116 | 21.570 | 17.02 |
| 3.869 | 22.965 | 36.43 |
| 3.565 | 24.950 | 11.58 |
| 3.337 | 26.690 | 6.65 |
| 3.125 | 28.531 | 11.60 |
| 2.993 | 29.823 | 3.93 |
| 2.778 | 32.194 | 4.65 |
| 2.718 | 32.918 | 4.19 |
| 2.619 | 34.196 | 3.28 |
| 2.551 | 35.140 | 2.52 |
| 2.482 | 36.151 | 1.83 |
| 2.391 | 37.578 | 1.77 |
| 2.245 | 40.129 | 0.69 |
| 2.077 | 43.534 | 0.94 | comprising, reaction of a solution of perindopril of formula (I),

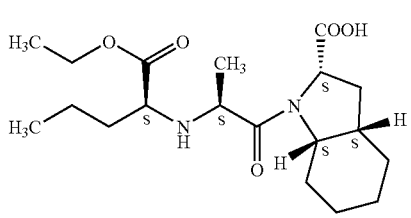

in a solvent selected from N,N-dimethylformamide, dimethyl acetals of lower aliphatic aldehydes, dimethyl ketals of lower aliphatic ketones and 1,2-dialkoxyethane with tertiary butylamine and crystallization of the erbumine salt thus obtained by heating the reaction mixture to reflux, filtering hot to remove any insoluble or suspended matter, cooling to 20° C. to 30° C. and further cooling to 0° C. to 15° C. for 30 minutes to 1 hour and finally filtering off and drying the crystals.

DESCRIPTION OF THE DRAWINGS, DETAILS OF INSTRUMENTS, AND DETAILS OF METHOD OF ANALYSIS AND PREPARATION OF SAMPLES

Figure 1:
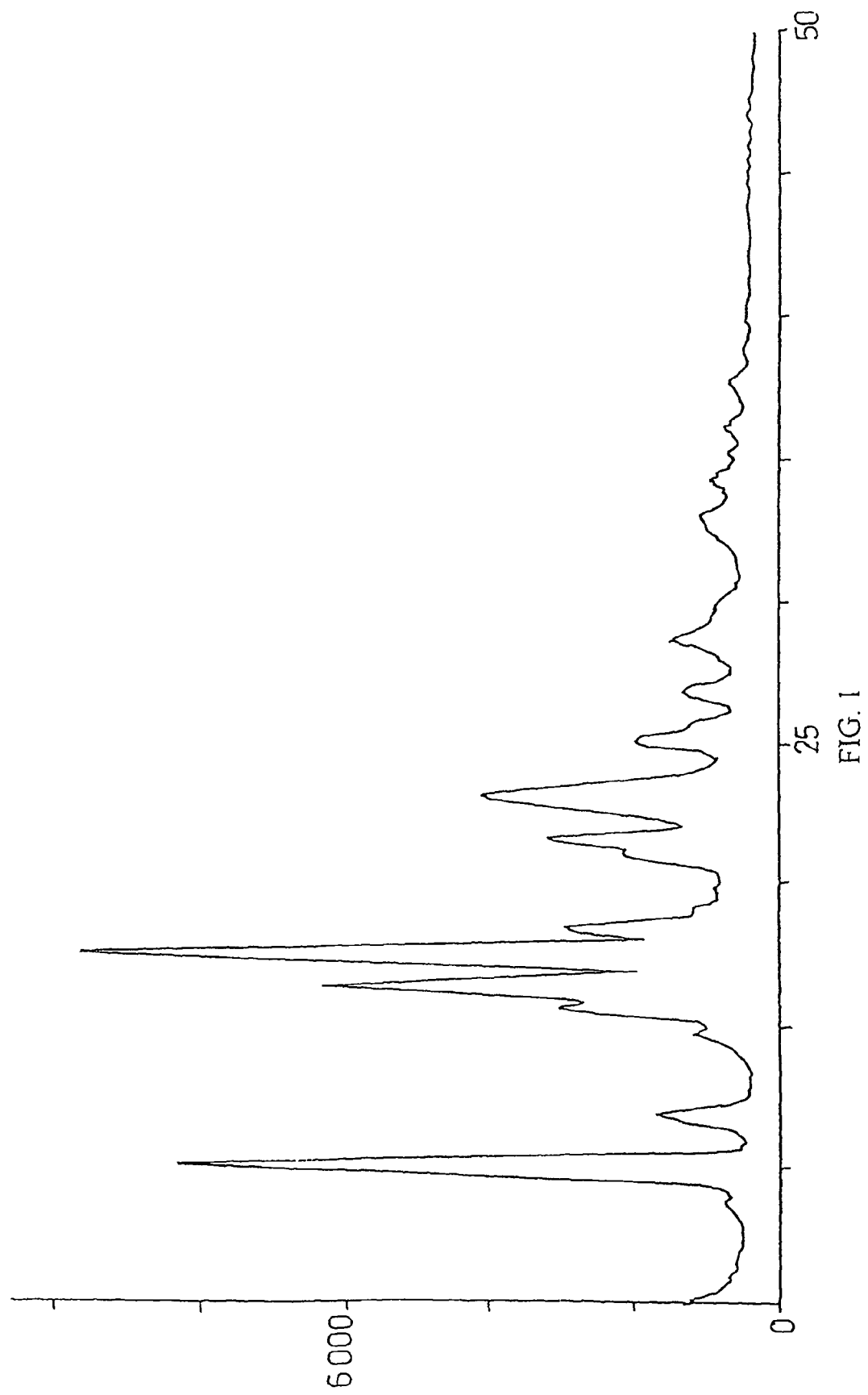

FIG. 1: X-ray (powder) diffraction pattern of perindopril erbumine (II) prepared and crystallized from ethyl acetate, according to the method described in U.S. Pat. No. 4,914,214

FIG. 2: X-ray (powder) diffraction pattern of perindopril erbumine (II) prepared and crystallized from 2,2-dimethoxypropane according to the method of the present invention.

Figure 3:
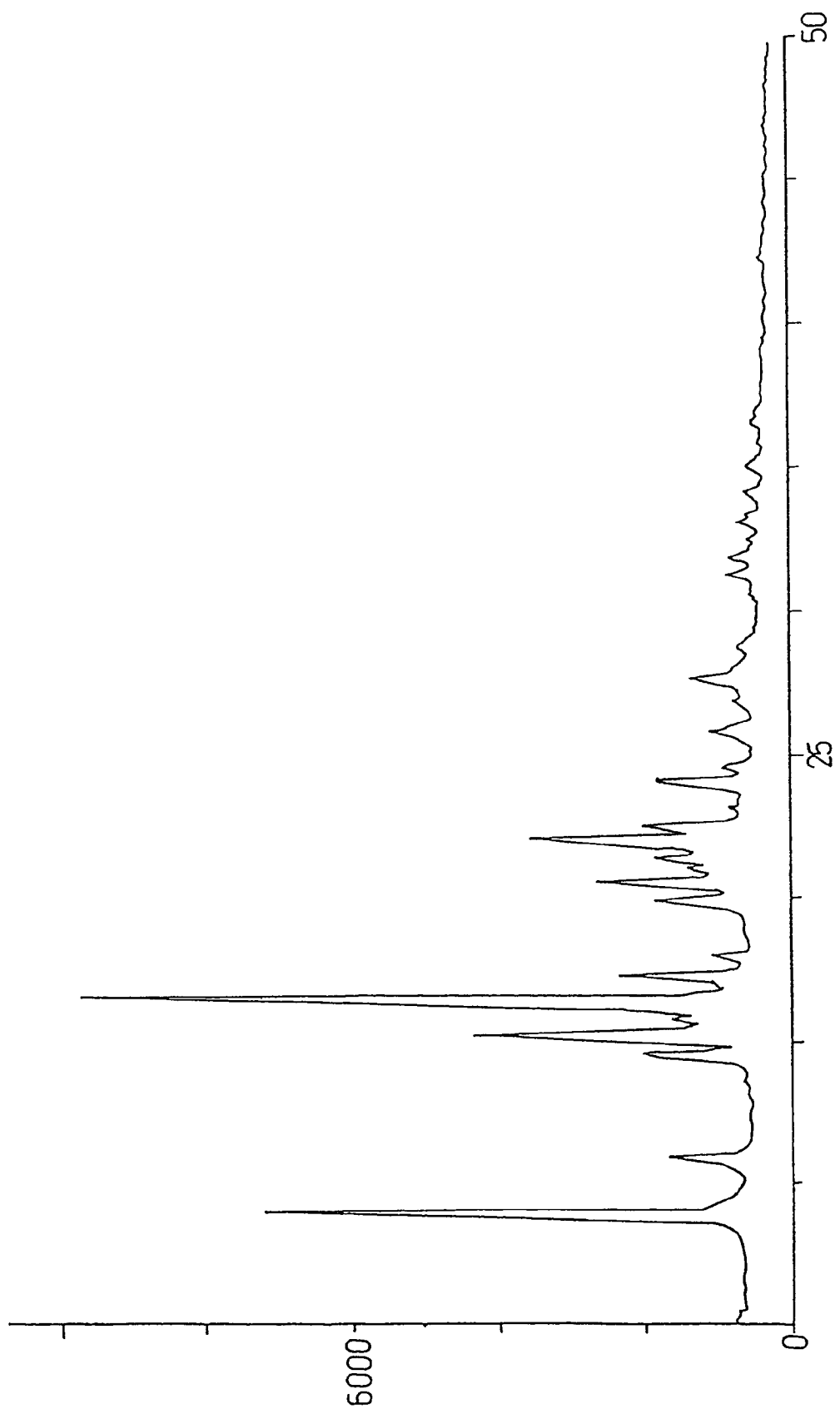

FIG. 3: X-ray (powder) diffraction pattern of perindopril erbumine (II) prepared and crystallized from 1,2-dimethoxyethane according to the method of the present invention.

Figure 4:
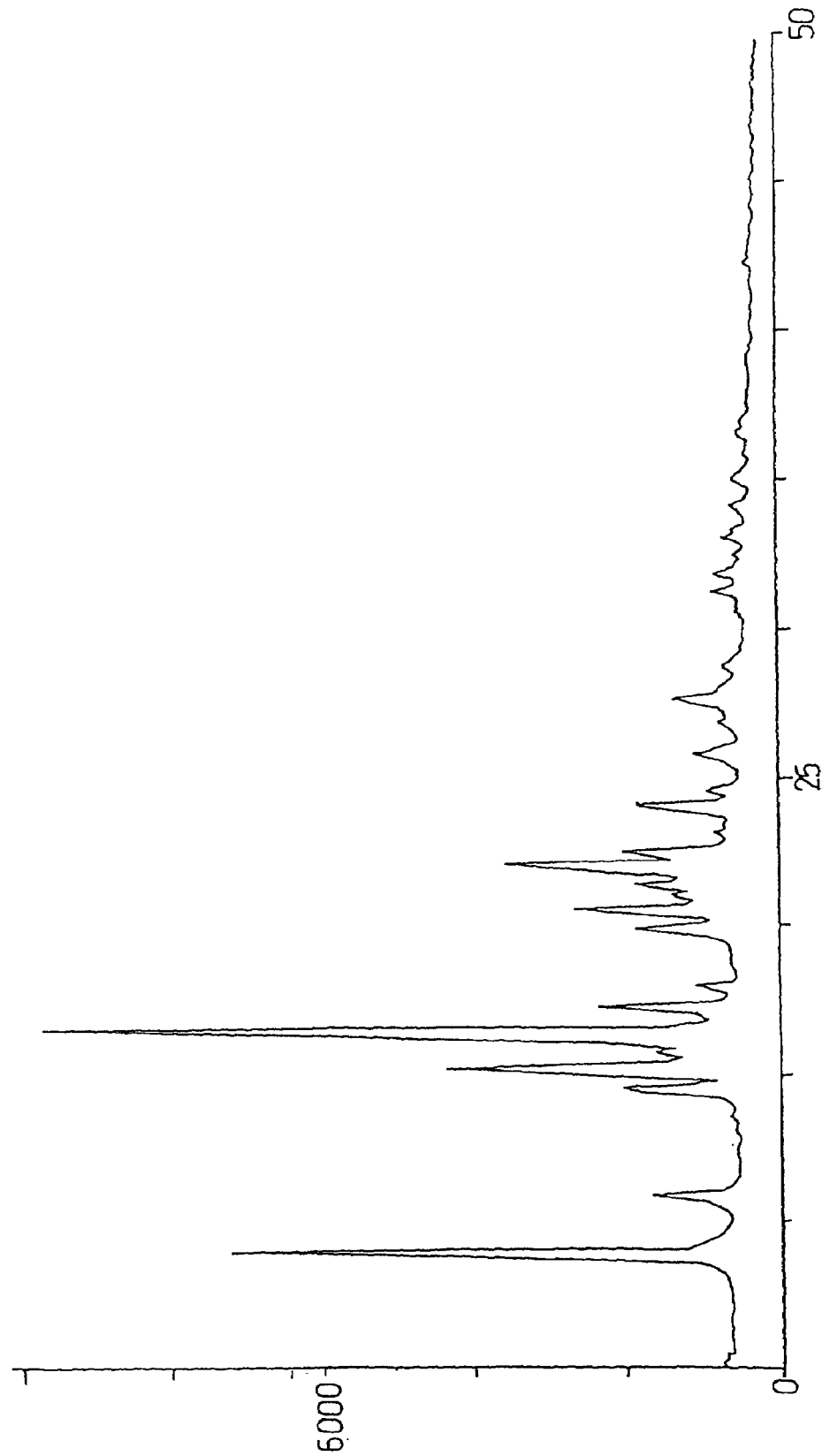

FIG. 4 X-ray (powder) diffraction pattern of perindopril erbumine (II) prepared and crystallized from dimethoxymethane according to the method of the present invention.

Figure 5:
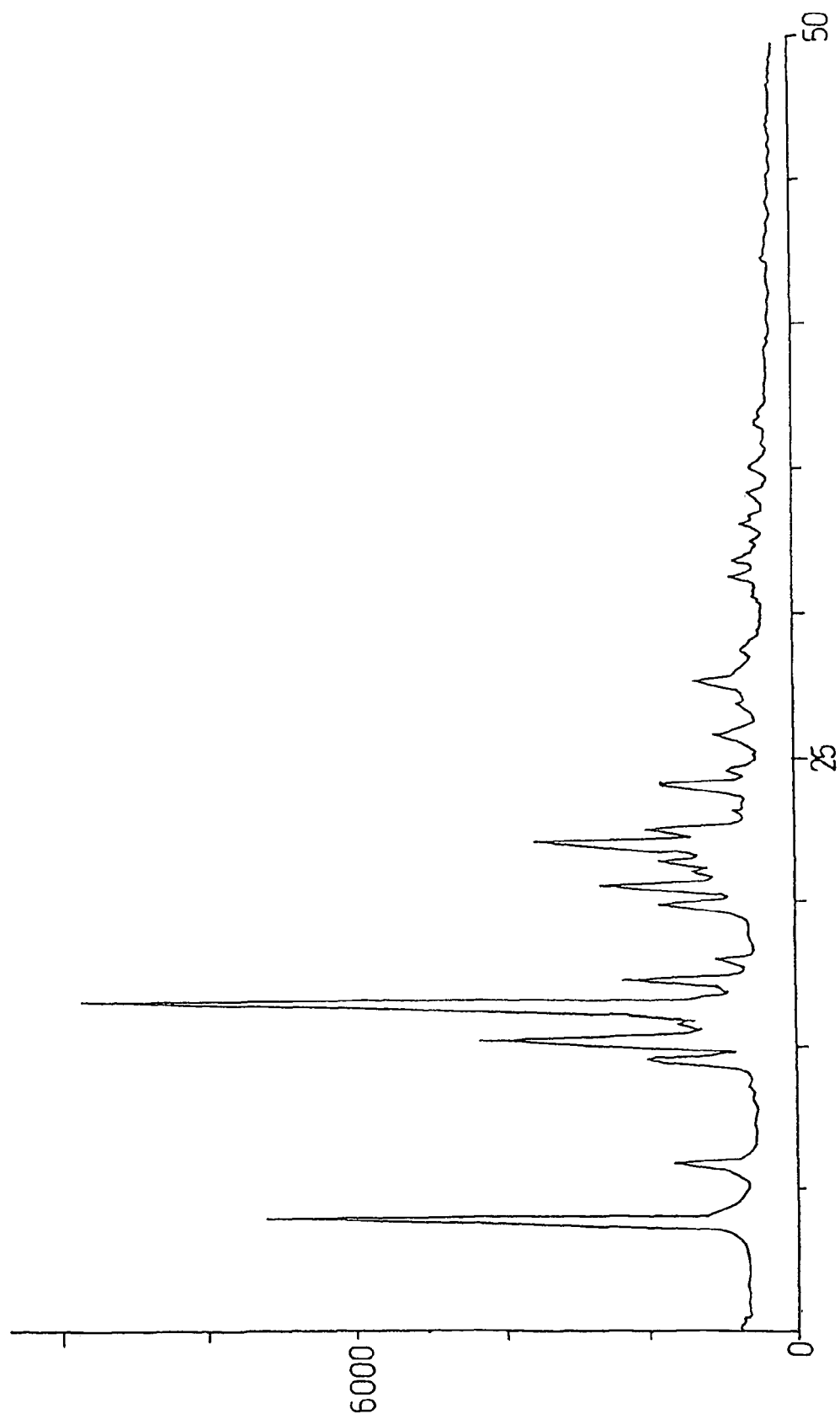

FIG. 5: X-ray (powder) diffraction pattern of perindopril erbumine (II) prepared and crystallized from N,N-dimethylformamide according to the method of the present invention.

FIG. 6: IR spectrum of perindopril erbumine (II) prepared and crystallized from ethyl acetate, according to the method described in U.S. Pat. No. 4,914,214.

Figure 7:
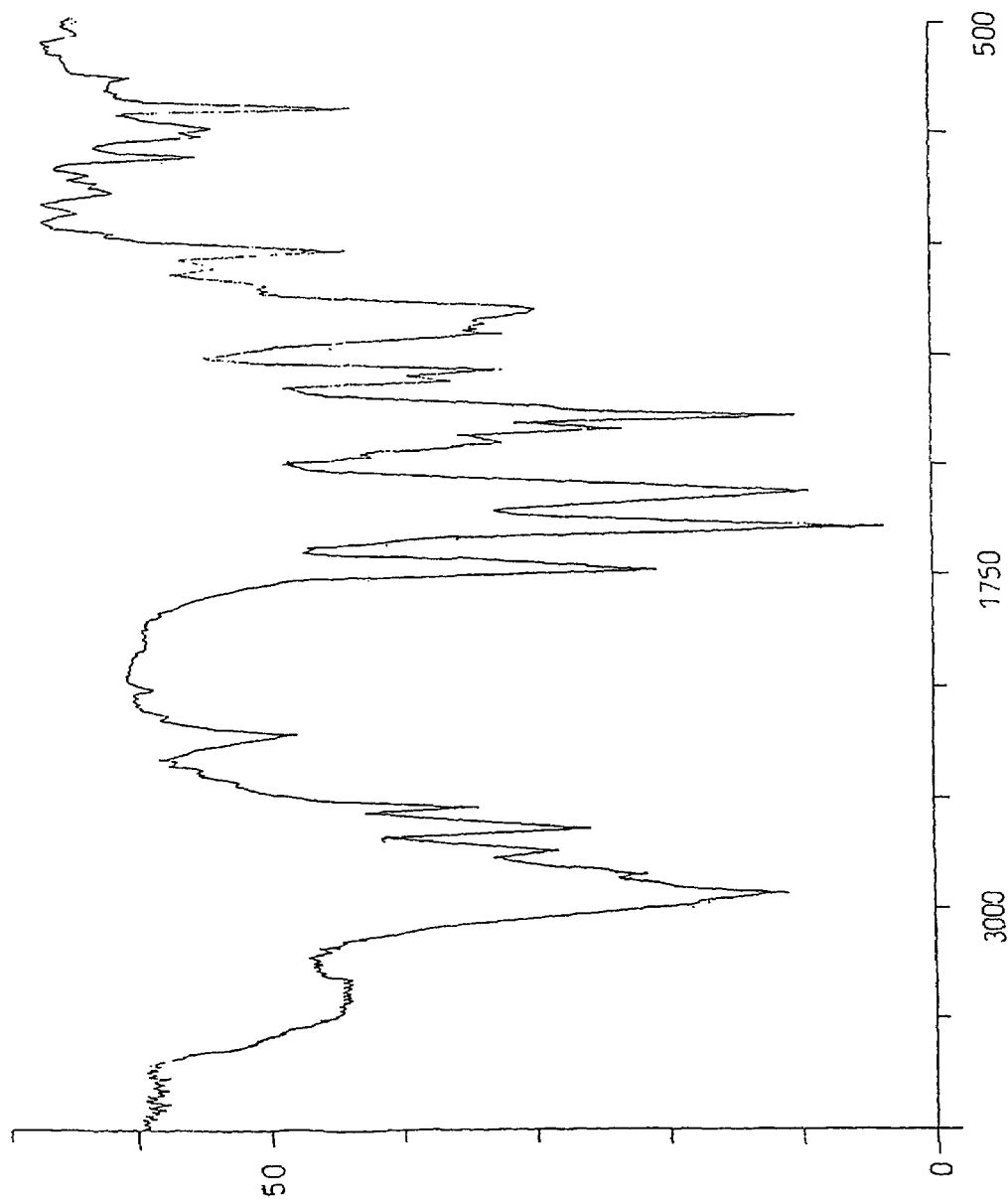

FIG. 7: IR spectrum of perindopril erbumine (II) prepared and crystallized from 2,2-dimethoxypropane according to the method of the present invention.

All IR spectra mentioned in this application were recorded on a Shimadzu 8201 PC FT IR instrument and the sample preparation was done on a KBr pellet.

All DSC thermograms mentioned in this application were recorded on a Mettler-Toledo SR instrument at a uniform heating rate of 2° C./minute of respective samples.

All X-ray (powder) diffraction patterns mentioned in this application were recorded on a Philips X'Pert PRO instrument using Bragg Brentano Reflection Geometry method with Cu target. The other details are given as under:

Wave length: K-alpha 1
K-alpha 1 wave length (Å): 1.5405600
K-alpha 2 wave length (Å): 1.5443900
K-alpha 2/K-alpha 1 intensity ratio: 0.5000
Initial angle ($2\theta$): 0°
Final angle ($2\theta$): 50°

DETAILED DESCRIPTION OF THE INVENTION

1. Preparation of Perindopril (I)

As mentioned hereinearlier, perindopril of formula (I) for conversion to perindopril erbumine of formula (II) can be prepared by any of the methods described in the prior art or by methods invented by the inventors, the details of which are given hereinbelow.

1(a): Preparation of Perindopril (I) as Per the Method Described in U.S. Pat. No. 4,914,214

Perindopril (I) was prepared exactly as per the method described in Example Stage 1a to 3C, columns 6 to 9 of U.S. Pat. No. 4,914,214 and as per the chemistry summarized in Scheme-I. The final product was isolated from a aqueous solution containing it by freeze-drying and the fluffy solid thus obtained was dried at 40-45° C. under vacuum to constant weight.

1(b): Preparation of Perindopril (I) as Per the Novel Method Invented by the Inventors and Disclosed in Our Pending PCT Application No. PCT/IN03/00042, Dated Feb. 28, 2003

In another method, perindopril (I) was prepared as per the novel method invented by the present inventors and disclosed in our pending PCT Application No. PCT/IN03/00042, dated Feb. 28, 2003 as per the chemistry summarized in Scheme-III.

The method essentially comprises reaction of L-norvalinate (C) with anyone of racemic 2-halo propionic acid benzyl ester of formula (D) and/or optically active (R)-2-halo propionic acid benzyl ester of formula (E), wherein X is chlorine or bromine in the presence of an organic solvent and in the presence of a base and obtaining therefrom the peptide compound, viz. N-[1(S)-ethoxycarbonyl-1-butyl]-(S)-alanine benzyl ester of formula (F). Removal of the benzyl protective group of said peptide compound of formula (F) through catalytic hydrogenation gives N-[1(S)-ethoxycarbonyl-1-butyl]-(S)-alanine of formula (G).

The N-[1(S)-ethoxycarbonyl-1-butyl]-(S)-alanine (G) thus obtained is converted to the acid chloride by reaction with a halogenating agent selected from thionyl chloride, phosphorous pentachloride, phosphorous trichloride, phosphorous oxychloride, oxalyl chloride etc. to give the corresponding acid chloride of formula (H).

The acid chloride (H) is reacted with the benzyl ester of (2S,3aS,7aS)-2-carboxyperhydroindole of formula (J) to give perindopril benzyl ester (K). Removal of the benzyl protective group gives perindopril (I), which is isolated from the reaction mixture by evaporation of the solvent in which the catalytic hydrogenolysis was carried out.

1(c): Preparation of Perindopril (I) as Per the Novel Method Invented by the Inventors and Disclosed in Our Pending PCT Application No. PCT/IN03/00257, Dated Jul. 31, 2003

In yet another method, perindopril (I) was prepared as per the novel method, utilizing a novel intermediate invented by the present inventors and disclosed in our pending PCT Application No. PCT/IN03/00257, Dated Jul. 31, 2003, the chemistry of which is summarized in Scheme-IV.

The method essentially involves utilization of a novel reactive derivative of N-[1(S)-ethoxycarbonyl-1-butyl]-(S)-alanine (G), viz. the 2'benzothiazolyl ester of formula (N), which in turn is prepared by reaction of N-[1(S)-ethoxycarbonyl-1-butyl]-(S)-alanine (G) with 2,2'-dithio bis[benzthiazol] of formula (L) or by reaction of N-[1(S)-ethoxycarbonyl-1-butyl]-(S)-alanine acid chloride of formula (H) with 2-mercaptobenzothiazole of formula (M).

The novel reactive derivative (N) is reacted with a carboxylic acid ester of (2S,3aS,7aS)-2-carboxyperhydroindole of formula (J) to give perindopril carboxylic acid ester (O). Removal of the benzyl protective group gives perindopril (I).

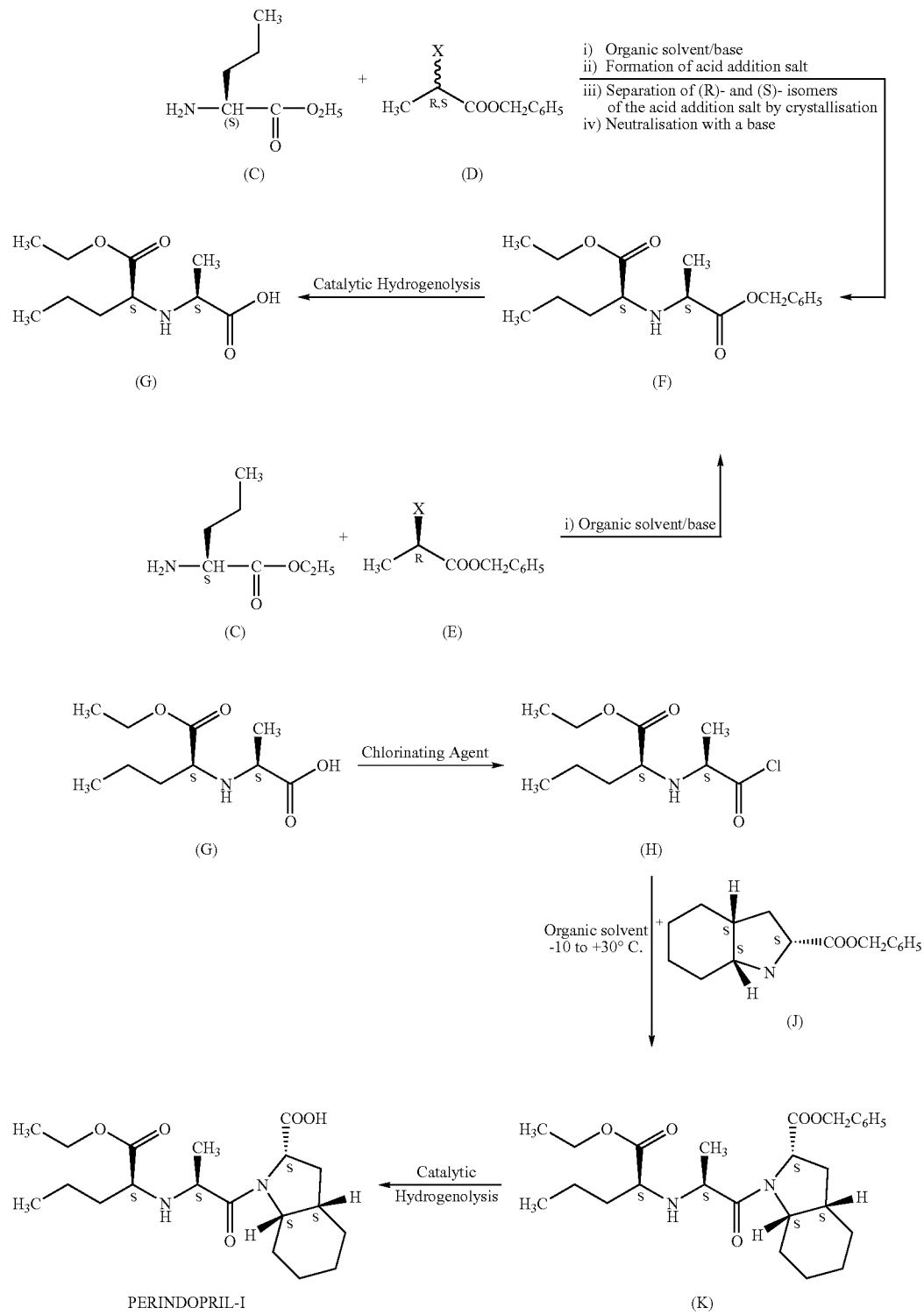
Scheme III
Synthesis of Perindopril in accordance with the preferred embodiment of our pending PCT Application No. IN/03/00042, date Feb. 28, 2003

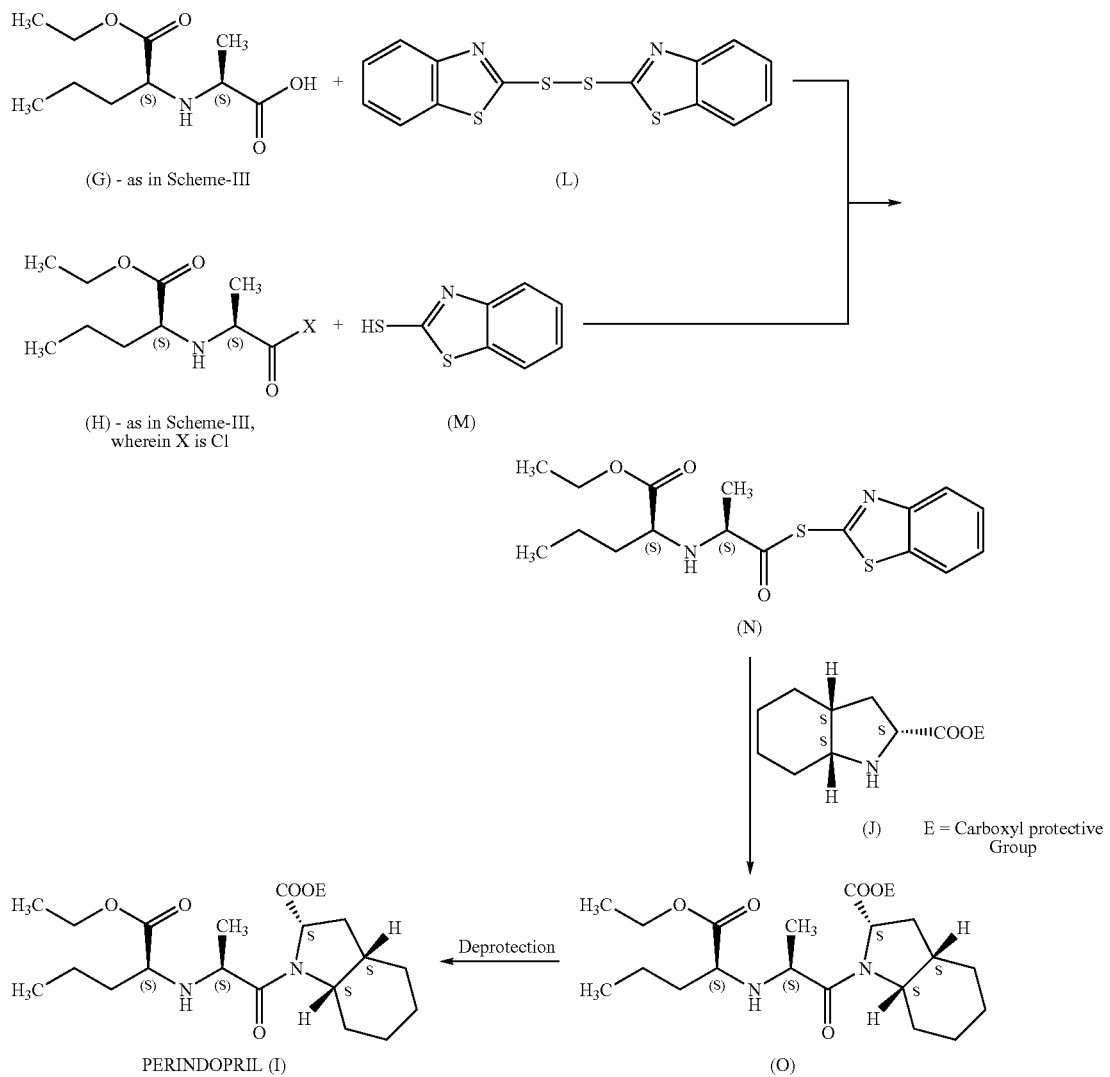

Scheme-IV:
Synthesis of Perindopril in accordance with the preferred embodiment of our pending PCT Application No. PCT/IN03/00257, dated Jul. 31, 2003

2. Preparation of Crystalline Perindopril Erbumine

Perindopril prepared by any of the methods mentioned hereinabove was converted to perindopril erbumine (II) and crystallized from N,N-dimethylformamide, dimethyl acetals of lower aliphatic aldehydes, dimethyl ketals of lower aliphatic ketones and 1,2-dialkoxyethane selected from dimethoxymethane, 1,2-dimethoxyethane and 2,2-dimethoxypropane as detailed hereinbelow.

2(a): Preparation of Perindopril Erbumine from Perindopril Obtained and Prepared as Per the Method Described in U.S. Pat. No. 4,914,214 and Crystallization of the Erbumine Salt from Ethyl Acetate Perindopril (I) prepared exactly as per the method described in Example Stage 1a to 3C, columns 6 to 9 of U.S. Pat. No. 4,914,214 and as per the chemistry summarized in Scheme-I was suspended in ethyl acetate to which was gradually added tertiary-butylamine. The mixture was heated to reflux till a clear solution was obtained and then filtered hot to remove any suspended particles. Thereafter, the solution was cooled to 25° C. to 30° C. and the crystallized solid was filtered and dried at 40-45° C. under vacuum for 5-6 hours to give crystalline perindopril erbumine (II), exhibiting the IR spectral values given in FIG. 6 and summarized hereinbelow IR (KBr; cm−1): 2931, 1747, 1643, 1566, 1392; DSC thermogram: endotherm at 135° C.; and the X-ray (powder) diffraction pattern summarized in Table-I and FIG. 1.

The IR spectrum, DSC thermogram and X-ray (powder) diffraction pattern of perindopril erbumine are identical and/or superimposable to that obtained and prepared as per the method described in U.S. Pat. No. 4,914,214 and crystallization of the erbumine salt from ethyl acetate, as summarized in Table-I and FIG. 1.

TABLE I

X-ray (powder) diffraction pattern of perindopril erbumine prepared and crystallized from ethyl acetate from perindopril prepared and obtained as per Example Stage 3D of U.S. Pat. No. 4,914,214

| d-spacing (Å) | Angle (° 2θ) | Relative Intensity (%) |
|---|---|---|
| 10.286 | 8.589 | 2.80 |
| 8.821 | 10.019 | 85.52 |
| 7.404 | 11.943 | 13.71 |
| 6.014 | 14.716 | 7.85 |
| 5.716 | 15.487 | 25.74 |
| 5.424 | 16.325 | 64.25 |
| 5.096 | 17.385 | 100.00 |
| 4.822 | 18.381 | 27.11 |
| 4.267 | 20.798 | 15.70 |
| 4.107 | 21.615 | 29.72 |
| 3.884 | 22.877 | 38.01 |
| 3.767 | 23.594 | 27.91 |
| 3.555 | 25.025 | 17.06 |
| 3.325 | 26.784 | 9.90 |
| 3.122 | 28.558 | 11.77 |
| 2.977 | 29.984 | 4.60 |
| 2.709 | 33.037 | 7.62 |
| 2.616 | 34.243 | 5.62 |
| 2.548 | 35.186 | 3.63 |
| 2.479 | 36.193 | 3.74 |
| 2.385 | 37.670 | 2.93 |
| 2.247 | 40.090 | 0.85 |
| 2.073 | 43.621 | 1.10 |

2(b): Preparation and Crystallization of Perindopril Erbumine from 1,4-dioxane from Perindopril Obtained and Prepared as Per the Method Described in U.S. Pat. No. 4,914,214

Perindopril (I) prepared exactly as per the method described in Example Stage 1a to 3C, columns 6 to 9 of U.S. Pat. No. 4,914,214 and as per the chemistry summarized in Scheme-I and as mentioned hereinbefore in Section 1 (a) was suspended in 1,4-dioxane (instead of ethyl acetate) to which was gradually tertiary-butylamine. The mixture was heated to reflux till a clear solution was obtained and filtered hot to remove any suspended particles. Thereafter, the solution was cooled to 25° C. to 30° C. and the crystallized solid was filtered and dried at 40-45° C. under vacuum for 5-6 hours to give crystalline perindopril erbumine (II), exhibiting the X-ray (powder) diffraction pattern summarized in Table-II.

The X-ray (powder) diffraction pattern is different from that obtained and prepared as per the method described in U.S. Pat. No. 4,914,214 and crystallization of the erbumine salt from ethyl acetate, as summarized in Table-I and FIG. 1.

TABLE II

X-ray (powder) diffraction pattern of perindopril erbumine prepared and crystallized from 1,4-dioxane from perindopril prepared and obtained as per Example Stage 3D of U.S. Pat. No. 4,914,214

| d-spacing (Å) | Angle (° 2θ) | Relative Intensity (%) |
|---|---|---|
| 10.015 | 8.822 | 100.00 |
| 8.242 | 10.724 | 12.01 |
| 6.125 | 14.448 | 42.23 |
| 5.806 | 15.247 | 96.26 |
| 5.445 | 16.265 | 94.68 |
| 5.171 | 17.130 | 32.99 |
| 4.499 | 19.714 | 30.82 |
| 4.300 | 52.81 | 20.634 |
| 4.069 | 21.821 | 57.62 |
| 3.974 | 22.347 | 43.92 |
| 3.730 | 23.832 | 37.45 |
| 3.464 | 25.692 | 15.32 |
| 3.273 | 27.218 | 13.76 |
| 3.161 | 28.204 | 12.08 |
| 2.822 | 31.673 | 6.61 |
| 2.701 | 33.129 | 7.08 |
| 2.557 | 35.055 | 6.14 |
| 2.465 | 36.410 | 2.85 |

2(c): Preparation and Crystallization of Perindopril Erbumine from Acetonitrile from Perindopril Obtained and Prepared as Per the Method Described in U.S. Pat. No. 4,914,214

Perindopril (I) prepared exactly as per the method described in Example Stage 1a to 3C, columns 6 to 9 of U.S. Pat. No. 4,914,214 and as per the chemistry summarized in Scheme-I and as mentioned hereinbefore in Section 1 (a) was suspended in acetonitrile (instead of ethyl acetate) to which was gradually tertiary-butylamine. The mixture was heated to reflux till a clear solution was obtained and filtered hot to remove any suspended particles. Thereafter, the solution was cooled to 25° C. to 30° C. and the crystallized solid was filtered and dried at 40-45° C. under vacuum for 5-6 hours to give crystalline perindopril erbumine (II), exhibiting the X-ray (powder) diffraction pattern summarized in Table-III.

The X-ray (powder) diffraction pattern is different from that obtained and prepared as per the method described in U.S. Pat. No. 4,914,214 and crystallization of the erbumine salt from ethyl acetate, as summarized in Table-I and FIG. 1.

TABLE III

X-ray (powder) diffraction pattern of perindopril erbumine prepared and crystallized from acetonitrile from perindopril prepared and obtained as per Example Stage 3D of U.S. Pat. No. 4,914,214

| d-spacing (Å) | Angle (° 2θ) | Relative Intensity (%) |
|---|---|---|
| 9.736 | 9.075 | 51.00 |
| 9.307 | 9.494 | 29.79 |
| 8.231 | 10.738 | 9.06 |
| 6.134 | 14.426 | 21.81 |
| 5.774 | 15.331 | 69.73 |
| 5.442 | 16.273 | 100.00 |
| 5.112 | 17.332 | 21.34 |
| 4.488 | 19.760 | 18.00 |
| 4.288 | 59.95 | 20.695 |
| 4.219 | 21.038 | 53.96 |
| 4.064 | 21.851 | 49.89 |
| 3.715 | 23.930 | 23.69 |
| 3.424 | 25.994 | 12.70 |
| 3.249 | 27.422 | 11.18 |
| 2.831 | 31.572 | 5.29 |
| 2.550 | 35.161 | 2.75 |
| 2.448 | 36.673 | 3.03 |

2(d): Preparation and Crystallization of Perindopril Erbumine from 2,2-dimethoxypropane from Perindopril Obtained and Prepared as Per the Method Described in U.S. Pat. No. 4,914,214

Perindopril (I) prepared exactly as per the method described in Example Stage 1a to 3C, columns 6 to 9 of U.S. Pat. No. 4,914,214 and as per the chemistry summarized in Scheme-I and as mentioned hereinbefore in Section 1 (a) was suspended in 2,2-dimethoxypropane (instead of ethyl acetate) to which was gradually tertiary-butylamine. The mixture was heated to reflux till a clear solution was obtained and filtered hot to remove any suspended particles. Thereafter, the solution was cooled to 20° C. to 30° C., and then further cooled to 0° C. to 15° C., maintained at the same temperature for 30 minutes to 1 hour and finally the crystallized solid was filtered and dried at 40-45° C. under vacuum for 5-6 hours to give crystalline perindopril erbumine (II), exhibiting IR spectra values and, DSC thermogram summarized hereinbelow IR(KBr; cm−1): 2931, 1747, 1643, 1566, 1392; DSC thermogram: endotherm at 135° C.; and X-ray (powder) diffraction pattern summarized in Table-IV and FIG. 2

The IR spectrum, DSC thermogram and X-ray (powder) diffraction pattern of perindopril erbumine are identical and/or superimposable to that obtained and prepared as per the method described in U.S. Pat. No. 4,914,214 and crystallization of the erbumine salt from ethyl acetate, as summarized in Table-I and FIG. 1.

TABLE IV

X-ray (powder) diffraction pattern of perindopril erbumine prepared and crystallized from 2,2-dimethoxypropane from perindopril prepared and obtained as per the present invention

| d-spacing (Å) | Angle (° 2θ) | Relative Intensity (%) |
| --- | --- | --- |
| 10.239 | 8.628 | 1.16 |
| 8.886 | 9.945 | 49.45 |
| 7.453 | 11.863 | 10.26 |
| 6.054 | 14.618 | 3.35 |
| 5.716 | 15.487 | 14.10 |
| 5.435 | 16.294 | 33.06 |
| 5.082 | 17.434 | 100.00 |
| 4.844 | 18.296 | 14.06 |
| 4.661 | 19.023 | 5.88 |
| 4.278 | 20.744 | 8.50 |
| 4.116 | 21.570 | 17.02 |
| 3.869 | 22.965 | 36.43 |
| 3.565 | 24.950 | 11.58 |
| 3.337 | 26.690 | 6.65 |
| 3.125 | 28.531 | 11.60 |
| 2.993 | 29.823 | 3.93 |
| 2.778 | 32.194 | 4.65 |
| 2.718 | 32.918 | 4.19 |
| 2.619 | 34.196 | 3.28 |
| 2.551 | 35.140 | 2.52 |
| 2.482 | 36.151 | 1.83 |
| 2.391 | 37.578 | 1.77 |
| 2.245 | 40.129 | 0.69 |
| 2.077 | 43.534 | 0.94 |

2(e): Preparation and Crystallization of Perindopril Erbumine from Ethyl Acetate from Perindopril Obtained and Prepared as Per the Method Described in Our Pending PCT Application No. PCT/IN03/00042, Dated Feb. 28, 2003

Perindopril (I) prepared exactly as per the method described in our pending PCT Application No. PCT/IN03/00042, dated Feb. 28, 2003 and as per the chemistry summarized in Scheme-II and as mentioned hereinbefore in Section 1 (b) was suspended in ethyl acetate to which was gradually tertiary-butylamine. The mixture was heated to reflux till a clear solution was obtained and filtered hot to remove any suspended particles. Thereafter, the solution was cooled to 20° C. to 30° C. and then further cooled to 0° C. to 15° C., maintained at the same temperature for 30 minutes to 1 hour and finally the crystallized solid was filtered and dried at 40-45° C. under vacuum for 5-6 hours to give crystalline perindopril erbumine (II), exhibiting the IR spectral values given in FIG. 6 and summarized hereinbelow IR spectrum (KBr; cm−1): 2931, 1747, 1643, 1566, 1392; DSC thermogram: endotherm at 135° C.; and the X-ray (powder) diffraction pattern summarized in Table-I and FIG. 1; and The IR spectrum, DSC thermogram and X-ray (powder) diffraction pattern of perindopril erbumine are identical and/or superimposable to that obtained and prepared as per the method described in U.S. Pat. No. 4,914,214 and crystallization of the erbumine salt from ethyl acetate, as summarized in Table-I and FIG. 1.

2(f): Preparation and Crystallization of Perindopril Erbumine from 2,2-dimethoxypropane from Perindopril Obtained and Prepared as Per the Method Described in Our Pending PCT Application No. PCT/IN03/00042, Dated Feb. 28, 2003

Perindopril (I) prepared exactly as per the method described in our pending PCT Application No. PCT/IN03/00042, dated Feb. 28, 2003 and as per the chemistry summarized in Scheme-II and as mentioned hereinbefore in Section 1 (b) was suspended in 2,2-dimethoxypropane (instead of ethyl acetate) to which was gradually tertiary-butylamine. The mixture was heated to reflux till a clear solution was obtained and filtered hot to remove any suspended particles. Thereafter, the solution was cooled to 20° C. to 30° C., and then further cooled to 0° C. to 15° C., maintained at the same temperature for 30 minutes to 1 hour and finally the crystallized solid was filtered and dried at 40-45° C. under vacuum for 5-6 hours to give crystalline perindopril erbumine (IU), exhibiting IR spectra values and, DSC thermogram summarized hereinbelow IR (KBr; cm−1): 2931, 1747, 1643, 1566, 1392; DSC thermogram: endotherm at 135° C.; and X-ray (powder) diffraction pattern summarized in Table-IV and FIG. 2

The IR spectrum, DSC thermogram and X-ray (powder) .diffraction pattern of perindopril erbumine are identical and/or superimposable to that obtained and prepared as per the method described in U.S. Pat. No. 4,914,214 and crystallization of the erbumine salt from ethyl acetate, as summarized in Table-I and FIG. 1.

2(g): Preparation and Crystallization of Perindopril Erbumine from 1,2-dimethoxyethane from Perindopril Obtained and Prepared as Per the Method Described in Our Pending PCT Application No. PCT/IN03/00042, Dated Feb. 28, 2003

Perindopril (I) prepared exactly as per the method described in our pending PCT Application No. PCT/IN03/00042, dated Feb. 28, 2003 and as per the chemistry summarized in Scheme-II and as mentioned hereinbefore in Section 1 (b) was suspended in 1,2-dimethoxyethane (instead of ethyl acetate) to which was gradually tertiary-butylamine. The mixture was heated to reflux till a clear solution was obtained and filtered hot to remove any suspended particles. Thereafter, the solution was cooled to 20° C. to 30° C., and then further cooled to 0° C. to 15° C., maintained at the same temperature for 30 minutes to 1 hour and finally the crystallized solid was filtered and dried at 40-45° C. under vacuum for 5-6 hours to give crystalline perindopril erbumine (II), exhibiting IR spectra values and, DSC thermogram summarized hereinbelow IR (KBr; cm−1): 2931, 1747, 1643, 1566, 1392; DSC thermogram: endotherm at 135° C.; and X-ray (powder) diffraction pattern summarized in Table-IV and FIG. 3

The IR spectrum, DSC thermogram and X-ray (powder) diffraction pattern of perindopril erbumine are identical and/or superimposable to that obtained and prepared as per the method described in U.S. Pat. No. 4,914,214 and crystallization of the erbumine salt from ethyl acetate, as summarized in Table-I and FIG. 1.

2(h): Preparation and Crystallization of Perindopril Erbumine from Dimethoxymethane ane from Perindopril Obtained and Prepared as Per the Method Described in Our Pending PCT Application No. PCT/IN03/00042, Dated Feb. 28, 2003

Perindopril (I) prepared exactly as per the method described in our pending PCT Application No. PCT/IN03/00042, dated Feb. 28, 2003 and as per the chemistry summarized in Scheme-II and as mentioned hereinbefore in Section 1 (b) was suspended in dimethoxymethane (instead of ethyl acetate) to which was gradually tertiary-butylamine. The mixture was heated to reflux till a clear solution was obtained and filtered hot to remove any suspended particles. Thereafter, the solution was cooled to 20° C. to 30° C., and then further cooled to 0° C. to 15° C., maintained at the same temperature for 30 minutes to 1 hour and finally the crystallized solid was filtered and dried at 40-45° C. under vacuum for 5-6 hours to give crystalline perindopril erbumine (II), exhibiting IR spectra values and, DSC thermogram summarized hereinbelow IR (KBr; cm−1): 2931, 1747, 1643, 1566, 1392; DSC thermogram: endotherm at 135° C.; and X-ray (powder) diffraction pattern summarized in Table-IV and FIG. 4

The IR spectrum, DSC thermogram and X-ray (powder) diffraction pattern of perindopril erbumine are identical and/or superimposable to that obtained and prepared as per the method described in U.S. Pat. No. 4,914,214 and crystallization of the erbumine salt from ethyl acetate, as summarized in Table-I and FIG. 1.

2(i): Preparation and Crystallization of Perindopril Erbumine from N,N-dimethylformamide from Perindopril Obtained and Prepared as Per the Method Described in Our Pending PCT Application No. PCT/IN03/00042, Dated Feb. 28, 2003

Perindopril (I) prepared exactly as per the method described in our pending PCT Application No. PCT/IN03/00042, dated Feb. 28, 2003 and as per the chemistry summarized in Scheme-II and as mentioned hereinbefore in Section 1 (b) was suspended in N,N-dimethylformamide (instead of ethyl acetate) to which was gradually tertiary-butylamine. The mixture was heated to reflux till a clear solution was obtained and filtered hot to remove any suspended particles. Thereafter, the solution was cooled to 20° C. to 30° C., and then further cooled to 0° C. to 15° C., maintained at the same temperature for 30 minutes to 1 hour and finally the crystallized solid was filtered and dried at 40-45° C. under vacuum for 5-6 hours to give crystalline perindopril erbumine (II), exhibiting IR spectra values and, DSC thermogram summarized hereinbelow IR (KBr; cm−1): 2931, 1747, 1643, 1566, 1392; DSC thermogram: endotherm at 135° C.; and X-ray (powder) diffraction pattern summarized in Table-IV and FIG. 5

The IR spectrum, DSC thermogram and X-ray (powder) diffraction pattern of perindopril erbumine are identical and/or superimposable to that obtained and prepared as per the method described in U.S. Pat. No. 4,914,214 and crystallization of the erbumine salt from ethyl acetate, as summarized in Table-I and FIG. 1.

2(j): Preparation and Crystallization of Perindopril Erbumine from Ethyl Acetate from Perindopril Obtained and Prepared as Per the Method Described in Our Pending PCT Application No. PCT/IN03/00257, Dated Jul. 31, 2003

Perindopril (I) prepared exactly as per the method described in our pending Application No. PCT/IN03/00257, dated Jul. 31, 2003 and as per the chemistry summarized in Scheme-III and as mentioned hereinbefore in Section 1 (c) was suspended in ethyl acetate to which was gradually tertiary-butylamine. Thereafter, the solution was cooled to 20° C. to 30° C. and then further cooled to 0° C. to 15° C., maintained at the same temperature for 30 minutes to 1 hour and finally the crystallized solid was filtered and dried at 40-45° C. under vacuum for 5-6 hours to give crystalline perindopril erbumine (II), exhibiting the IR spectral values given in FIG. 6 and summarized hereinbelow IR (KBr; cm−1): 2931, 1747, 1643, 1566, 1392; DSC thermogram: endotherm at 135° C.; and the X-ray (powder) diffraction pattern summarized in Table-I and FIG. 1; and The IR spectrum, DSC thermogram and X-ray (powder) diffraction pattern of perindopril erbumine are identical and/or superimposable to that obtained and prepared as per the method described in U.S. Pat. No. 4,914,214 and crystallization of the erbumine salt from ethyl acetate, as summarized in Table-I and FIG. 1.

2(k): Preparation and Crystallization of Perindopril Erbumine from 2,2-dimethoxypropane from Perindopril Obtained and Prepared as Per the Method Described in Our Pending PCT Application No. PCT/IN03/00257, Dated Jul. 31, 2003.

Perindopril (I) prepared exactly as per the method described in our pending PCT Application No PCT/IN03/00257 dated Jul. 31, 2003 and as per the chemistry summarized in Scheme-III and as mentioned hereinbefore in Section 1 (c) was suspended in 2,2-dimethoxypropane (instead of ethyl acetate) to which was gradually tertiary-butylamine. The mixture was heated to reflux till a clear solution was obtained and filtered hot to remove any suspended particles. Thereafter, the solution was cooled to 20° C. to 30° C., and then further cooled to 0° C. to 15° C., maintained at the same temperature for 30 minutes to 1 hour and finally the crystallized solid was filtered and dried at 40-45° C. under vacuum for 5-6 hours to give crystalline perindopril erbumine (II), exhibiting IR spectra values and, DSC thermogram summarized hereinbelow IR (KBr; cm−1):2931, 1747, 1643, 1566, 1392; DSC thermogram: endotherm at 135° C.; and X-ray (powder) diffraction pattern summarized in Table-IV and FIG. 2

The IR spectrum, DSC thermogram and X-ray (powder) diffraction pattern of perindopril erbumine are identical and/ or superimposable to that obtained and prepared as per the method described in U.S. Pat. No. 4,914,214 and crystallization of the erbumine salt from ethyl acetate, as summarized in Table-I and FIG. 1.

The above results clearly reveal that perindopril (I) prepared by any method and converted to perindopril erbumine (II) in a solvent selected from N,N-dimethylformamide and dimethyl acetals of lower aliphatic aldehydes, dimethyl ketals of lower aliphatic ketones and 1,2-dialkoxyethane and crystallized from the said solvent(s) gives crystalline perindopril erbumine (II), possessing a X-ray (powder) diffraction pattern, IR spectrum and DSC spectrum identical and/or superimposable with the crystalline form of perindopril erbumine obtained by crystallization from ethyl acetate, as per the method described in U.S. Pat. No. 4,914,214.

In particular, the solvents utilized in the present invention for crystallization of perindopril erbumine i. e. N,N-dimethylformamide, dimethyl acetals of lower aliphatic aldehydes, dimethyl ketals of lower aliphatic ketones and 1,2-dialkoxyethane unlike those used in the prior art, such as acetonitrile, 1,4-dioxane, dichloromethane, chloroform etc. are tolerated better by International Conference on Harmonization (ICH), and thereby rendering the process more amenable for commercial manufacture from a safety, environmental and regulatory point of view.

Further, perindopril erbumine obtained from crystallization of perindopril erbumine from N,N-dimethylformamide, dimethyl acetals of lower aliphatic aldehydes, dimethyl ketals of lower aliphatic ketones and 1,2-dialkoxyethane was found to possess improved physical characteristics like Particle Size, Flowability or Compressability Index etc. compared to the material obtained by crystallization from ethyl acetate. These characteristics result in improved dissolution profile, which in turn, results in improved bioavailability, thereby rendering the crystalline perindopril erbumine obtained by the process of the present invention more amenable for formulation into a suitable dosage form. These advantages form the basis of the present invention.

A comparison of the Compressibility Index and Particle Size Distribution of crystalline perindopril erbumine (II), obtained as per the method of the present invention with that obtained by crystallization from ethyl acetate as per the method disclosed in U.S. Pat. No. 4,914,214 is summarized in Table-IV.

TABLE IV

A comparison of the Compressibility Index and Particle Size Distribution of crystalline perindopril erbumine (II), obtained as per the method of the present invention with that obtained by crystallization from ethyl acetate as per the method disclosed in U.S. Pat. No. 4,914,214

| No. | Physical characteristic | Perindopril erbumine crystallized as per the method of the present invention | Perindopril erbumine crystallized as per the method of U.S. pat. ser. no. 4 914 214 from ethyl acetate |
|---|---|---|---|
| 01 | Compressibility Index | 23.8 | 20.00 |
| 02 | Particle Size Distribution | 9.06µ (10%); 36.37µ (50%); 119.78µ (90%) | 16.39µ (10%); 70.18µ (50%); 188.11µ (90%) |

Compressability Index, or in other words the Flowability of the two materials were determined by standard methods practiced in the art. The Particle Size Distribution was determined using a Mastersizer 2000, Version 2 instrument with cyclohexane as the dispersant.

It must be reiterated that minor and insignificant differences in X-ray (powder) diffraction pattern is common and these differences are not taken into consideration for drawing conclusions about similarity or differences of the crystal nature of a substance. For instance, it is well known in the art that said minor or insignificant differences could arise due to
i) type of instrument used,
ii) method used for preparing the sample,
iii) the operator variability i. e. the differences arising due to change in the operator handling the instrument etc.

The invention is further illustrated by the following non-limiting examples, which, however, should not be construed as limiting the scope of the invention.

REFERENCE EXAMPLE-1

Preparation of Perindopril (II) as Per the Method Disclosed in U.S. Pat. No. 4,914,214 and Summarized in Scheme-I The procedure described in the Example Stage 1a to Stage 3A, columns 6-8 of U.S. Pat. No. 4,914,214 was carried out exactly in identical fashion to prepare N-[(S)-1-carbethoxybutyl]-(S)-alanine and para toluenesulfonate of the benzyl ester of (2S,3aS,7aS)-2-carboxyoctahydroindole.

The above two compounds were reacted exactly as per the method described in Example Stage 3B and 3C; columns 8-9 of U.S. Pat. No. 4,914,214 to give perindopril benzyl ester and perindopril respectively, the details of which are given hereinbelow.

Step 1: Preparation of Perindopril Benzyl Ester

Triethyl amine (14 g, 0.1238 moles) was added to a suspension of (2S,3aS,7aS)-octahydroindole-2-carboxylic acid-benzyl ester para toluene sulfonate (20 g, 0.0464 moles) in ethyl acetate (240 g), under stirring at 25° C. in one lot. Then 1-hydroxybenzotriazole (24 g, 0.1776 moles), N-[(S)-1-carbethoxybutyl]-(S)-alanine (30 g, 0.1382 moles) were added to the reaction mixture at 25° C., under stirring, followed by dicyclohexyl carbodiimide (28 g, 0.1357 moles) at ambient temperature. The reaction mixture was stirred, keeping the temperature in the range of 15-20° C. for 3 hrs, when the TLC and the HPLC indicated a completion of the reaction. The reaction mixture was then filtered to remove the precipitated dicyclohexyl urea. The filtrate was washed with water (100 ml, twice). The organic layer was dried over sodium sulphate and concentrated under reduced pressure to afford a viscous oil, which was still contaminated with dicyclohexyl urea. The oil was redissolved in ethyl acetate (100 ml) and the solution was cooled to 2-5° C. under stirring for 1 hr. The precipitated dicyclohexyl urea was again filtered off and the filtrate was concentrated under reduced pressure to afford 20 g (94%) of perindopril benzyl ester as an oil.

Step 2: Preparation of Perindopril

The Perindopril benzyl ester (20 g, 0.0436 moles) was dissolved in cyclohexane (80 ml) in a round bottom flask and the resulting solution was transferred into a hydrogenation bottle. To this was added 10% Palladium on carbon (10% loading), followed by water (70 ml). The reaction mixture was hydrogenated at 27° C. for 3 hrs, under 60 psi pressure when the reaction was complete. The reaction mixture was filtered off and the residue was washed with cyclohexane (20 ml). The filtrate was allowed to settle for 15 min. The aqueous phase was separated. It was washed with cyclohexane (20 ml, twice). Perindopril was isolated in an amount of 11.5 g (71.5%) from the aqueous layer by freeze drying.

Example-1

Preparation of Perindopril (II) as Per the Method Disclosed in Our Pending PCT Application No. PCT/IN03/00042 and Summarized in Scheme-III Preparation of N-[1-(S)-ethoxycarbonyl-1-butyl]-(S)-alanine Method-I Step I: Preparation of N-[1-(S)-ethoxycarbonyl-1-butyl]-(R,S)-alanine benzyl ester To a solution of ethyl-L-norvalinate (IV, 62 g, 0.427 moles) in acetonitrile (300 ml) were added successively racemic (±)-benzyl-2-bromo-propionate (V, 125 g, 0.514 moles) and triethyl amine (178 ml, 1.282 moles). The reaction mixture was refluxed for 7-8 hrs. The excess solvent was removed by distillation under reduced pressure to afford a thick oil. The oil was dissolved in a mixture of diisopropyl ether (500 ml) and water (250 ml). The organic phase was extracted in 10% hydrochloric acid solution (250 ml×2). The combined acidic extracts were made alkaline by addition of an aqueous solution of sodium carbonate. The aqueous phase was again extracted with diisopropyl ether (200 ml×2). The combined organic layer was concentrated under reduced pressure to afford 103 g of the title compound as an oil.

IR: 1758 & 1728 cm$^{-1}$ $^1$H NMR (CDCl$_3$, δ): 0.65-1.5 (m, 13H, 2X—CH$_3$, C$_3$H$_7$); 2.00 (s, 1H, —NH—); 2.90-3.55 (m, 2X—CH—); 3.85 (q, 2H, —CH$_2$—); 5.2 (s, 2H, —CH$_2$—); 7.3 (m, 5H, ArH).

Step II: Preparation of Maleate Salt of N-[1-(S)-ethoxycarbonyl-1-butyl]-(S)-alanine benzy lester To a solution of the oil obtained in Step I (100 g, 0.325 moles) in acetone (250 ml) was added maleic acid (22.67 g, 0.195 moles). The solution was agitated and to it was added cyclohexane (600 ml). The reaction mixture was heated under reflux for 2.5-2 hrs, and then cooled gradually to 22-25° C. and then further to 0-5C. The solid crystallizing out was collected by filtration and dried at 45-50° C. under reduced pressure to give 42 g of maleate salt of N-[1-(S)-ethoxycarbonyl-1-butyl]-(S)-alanine benzyl ester. Recrystallization from a mixture of acetone and cyclohexane gave 38 g of the product having desired optical purity.

[α$_D^{20}$]: 18.8° (C=1/EtOH)

Melting point: 100° C.

$^1$H NMR (CDCl$_3$, δ): 0.95 (t, 3H, —CH$_3$); 1.25 (t, 3H, —CH$_3$); 1.5 (bq, 2H, —CH$_2$—); 1.6 (d, 3H, —CH$_3$); 1.8 (q, 2H, —CH$_2$—); 3.6 (t, 1H, —CH—); 3.8 (q, 1H, —CH—); 4.25 (q, 2H, —CH$_2$—); 5.25 (s, 1H, —CH$_2$—); 6.25 (s, 2H, —CH—); 7.30 (s, 5H, ArH); 9.00 (bs, 3H, —NH—, —COOH).

Step III: Preparation of N-[1-(S)-ethoxycarbonyl-1-butyl]-(S)-alanine benzyl ester To a suspension of the maleate salt obtained in Step II (23 g) in water (100 ml) and dichloromethane (200 ml), was added aqueous ammonia solution (25%) till pH of the reaction mixture remained constant in the range of 8.5-9.0. The organic layer was separated and concentrated in vacuum to afford 16 g the title compound as an oil.

[α$_D^{20}$]: 47.5° (C=1/EtOH)

$^1$H NMR (CDCl$_3$, δ): 0.95 (t, 3H, —CH$_3$); 1.25 (t, 3H, —CH$_3$); 1.5 (bq, 2H, —CH$_2$—); 1.6 (d, 3H, —CH$_3$); 1.8 (q, 2H, —CH$_2$—); 3.6 (t, 1H, —CH—); 3.8 (q, 1H, —CH—); 4.25 (q, 2H, —CH$_2$—); 5.25 (s, 1H, —CH$_2$—); 7.30 (s, 5H, ArH); 9.00 (bs, H, —NH—).

Step IV: Preparation of N-[1-(S)-ethoxycarbonyl-1-butyl]-(S)-alanine

A solution of the oil obtained in Step III (14.5 g) in absolute ethanol (150 ml) was hydrogenated in the presence of 10% palladised charcoal (0.8 g) under 40-45 psi pressure for 1.5-2 hrs. The reaction mixture was then concentrated under reduced pressure to afford a solid. This was dried at 40-45° C. under vacuum to give 8.7 g of the title compound.

[α$_D^{20}$]: 4.6° (C=1/EtOH)

Melting point: 148° C.

$^1$H NMR (DMSO-d$_6$, δ): 0.9 (t, 3H, —CH$_3$); 1.15 (t; 6H, 2X—CH$_3$); 1.2-1.4 (m, 2H, —CH$_2$); 1.45-1.6 (m, 2H, —CH$_2$—); 3.0-3.3 (m, 2H, 2X—CH—); 4.0-4.2 (q, 2H, —CH$_2$—).

Method-II

Step I: Preparation of N-[1-(S)-ethoxycarbonyl-1-butyl]-(S)-alanine benzyl ester To a solution of ethyl-L-norvalinate (IV, 62 g, 0.427 moles) in acetonitrile (300 ml) were added successively benzyl-(R)-2-bromo-propionate (V$^1$, 20 g, 0.0822 moles) and triethyl amine (28 ml, 0.2016 moles). The reaction mixture was refluxed for 7-8 hrs. The excess solvent was removed by distillation under reduced pressure to afford a thick oil. The oil was dissolved in a mixture of diisopropyl ether (80 ml) and water (40 ml). The organic phase was extracted in 10% hydrochloric acid solution (40 ml×2). The combined acidic extracts were made alkaline by addition of an aqueous solution of sodium carbonate. The aqueous phase was again extracted with diisopropyl ether (200 ml×2). The combined organic layer was concentrated under reduced pressure to afford 103 g of the title compound as an oil.

IR: 1758 & 1728 cm$^{-1}$ $^1$H N (CDCl$_3$, δ): 0.65-1.5 (m, 13H, 2X—CH$_3$, C$_3$H$_7$); 2.00 (s, 1H, —NH—); 2.90-3.55 (m, 2X—CH—); 3.85 (q, 2H, —CH$_2$—); 5.2 (s, 2H, —CH$_2$—); 7.3 (m, 5H, ArH).

Step-II: Preparation of N-[1-(S)-ethoxycarbonyl-1-butyl]-(S)-alanine

A solution of N-[1-(S)-ethoxycarbonyl-1-butyl]-(S)-alanine benzyl ester (14.5 g, as obtained in Step-I) in ethanol (150 ml) was hydrogenated in the presence of 10% palladised charcoal (0.8 g) under 40-45 psi hydrogen pressure for 1.5 to 2 hrs. The reaction mixture was concentrated under reduced pressure to give an oil. Crystallization from a mixture of acetonitrile and ethanol (1:3) gave 6.1 g the title compound $[\alpha_D^{20}]$: 4.6° (C=1/EtOH)

Melting point: 148° C.

$^1$H NMR (DMSO-d$_6$, δ): 0.9 (t, 3H, —CH$_3$); 1.15 (t, 6H, 2 X, —CH$_3$); 1.2-1.4 (m, 2H, —CH$_2$); 1.45-1.6 (m, 2H, —CH$_2$—); 3.0-3.3 (m, 2H, 2X—CH—); 4.0-4.2 (q, 2H, —CH$_2$—).

Step V: Preparation of N-[1-(S)-ethoxycarbonyl-1-butyl]-(S)-alanyl chloride

To a slurry of N-[1-(S)-ethoxycarbonyl-1-butyl]-(S)-alanine (1.5 g, 0.0069 moles, as obtained in Step-IV, Method-I and Step-II, Method-II) in n-hexane (10 ml) was purged dry hydrogen chloride gas at 25-30° C. under agitation. To this was added finely ground phosphorous pentachloride (1.8 g, 0.0086 moles) in four lots, each after an interval of 10 mns. After the complete addition the reaction mixture was agitated for 1.5 hrs. The solid precipitated was filtered, washed with hexane to give 1.88 g of the title compound (I).

IR ν cm$^{-1}$: 1741 and 1791

$^1$H NMR (DMSO-d$_6$, δ): 0.90 (3H, —CH$_3$); 1.15 (3H, t, —CH$_3$); 1.2-1.5 (5H, m, —CH$_2$, —CH$_3$); 1.5-1.9 (2H, m, —CH$_2$); 3.8-4.3 (4H, m, 2X—CH, —CH$_2$); 9.6 (1H, bs, —NH).

Step VI: Preparation of Perindopril Benzyl Ester

To a solution of (2S,3aS,7aS)-octahydroindole-2-carboxylic acid benzyl ester (1.6 g, 0.0062 moles) and triethylamine (2.9 ml, 0.0208 moles) in dichloromethane (10 ml) was added a slurry of N-[1-(S)-ethoxycarbonyl-1-butyl]-(S)-alanyl chloride (I, 1.88 g. 0.0069 moles) in dichloromethane 910 ml) at −10 to 15° C. over a period of 25-30 mns. After the complete addition the reaction temperature was gradually raised to 25-30° C. The reaction mixture was quenched with water (20 ml). The organic layer was separated, washed successively with 55 Hcl (10 ml×2 times), 105 aqueous sodium carbonate solution (10 ml×2 times) and water 910 ml×2 times). The organic layer was concentrated under reduced pressure at 40-45° C. to give 2.3 g of the benzyl ester.

Step VII: Preparation of Perindopril

Perindopril benzyl ester (1.4 g) obtained in Step VI was dissolved in absolute ethanol (15 ml). To the solution was added 10% Pd—C (5% w/w) and the mixture hydrogenated at 20-22° C. for 3 hours till completion of the reaction. The catalyst was filtered off and the filtrate concentrated under reduced pressure at 45° C. to give 1.3 g of perindopril (II).

Example-2

Preparation of Perindopril (II) as Per the Method Disclosed in Our Pending PCT Application No. PCT/IN03/00257 and Summarized in Scheme-IV Step I Preparation of N-[1(S)-ethoxycarbonyl-3-phenylpropyl]-(S)-alanine-2'-benzothiazolylthio ester Method-I Triphenyl phosphine (6.25 g, 0.023 moles) was dissolved in dichloromethane (60 ml) at a temperature of 25-30° C. 2,2'-Dithiobis(benzothiazole) (7.9 g, 0.023 moles) was added to the solution under stirring at the same temperature. The reaction mixture was stirred for 45 min. to 1 hr and then cooled to 0-5° C. To this was added N-[1(S)-ethoxycarbonyl-3-phenylpropyl]-(S)-alanine (5.54 g, 0.0198 moles) at the same temperature and the reaction mixture was stirred for 5-10 min. Triethylamine (3 ml) was then added and the reaction mixture stirred for 30-45 min. The temperature was raised to 25-30° C. and stirring was continued for 2-2.5 hrs. The reaction mixture was then concentrated at 35-40° C. under reduced pressure to give an oily mass. The oil was chromatographed over silica gel using a mixture of chloroform and petroleum ether (40-60° C.) as eluent (3:7) to give the pure title compound as an oil.

IR (cm$^{-1}$): 1732, 1600

$^1$H NMR (CDCl$_3$, δ): 1.30, t, 3H; 1.50, d, 3H; 1.90-2.30, m, 3H; 2.70-3.10, m, 2H; 3.40-3.70, m, 2H; 4.20, q, 2H; 7.10-7.60, m, 7H; 7.90, dd, 1H; 8.10, dd, 1H $^{13}$C NMR (CDCl$_3$, δ): 14.74, 20.45, 27.42, 32.66, 35.93, 61.64, 63.57, 112.39, 121.66, 123.29, 124.63, 125.77, 126.54, 126.63, 127.27, 128.89, 141.57, 175.18, 203.04

Method-II

Alternatively, to a solution of N-[1(S)-ethoxycarbonyl-3-phenylpropyl]-(S)-alanine (5 g, 17.9 mmoles) in cyclohexane (15 ml) was added phosphorous pentachloride (4.7 g, 22.5 mmoles) with simultaneous bubbling of HCl gas at 25-30° C. over a period of 1 hr. The reaction mixture containing the acid chloride hydrochloride of N-[1(S)-Ethoxycarbonyl-3-phenylpropyl]-(S)-alanine thus obtained was filtered under an atmosphere of nitrogen. The filtered solid was slurried in dichloromethane (30 ml). The slurry was added to a solution of 2-mercaptobenzothiazole (VI, 2.7 g, 16.2 mmoles) in dichloromethane (20 ml) containing triethylamine (7.5 ml, 53.8 mmoles) at 0 to −5° C. After the addition was complete the reaction mixture was stirred at 25-30° C. for 1 hr, till completion of the reaction as indicated by TLC. The reaction mixture was then concentrated under reduced pressure to afford a viscous residue, which was chromatographed over silica gel using a mixture of chloroform and petroleum ether (40-60° C.) as eluent (3:7) to give the pure title compound (3.0 g, 40%) as an oil.

IR (cm$^{-1}$): 1732, 1600

$^1$H NMR (CDCl$_3$, δ): 1.30, t, 3H; 1.50, d, 3H; 1.90-2.30, m, 3H; 2.70-3.10, m, 2H; 3.40-3.70, m, 2H; 4.20, q, 2H; 7.10-7.60, m, 7H; 7.90, dd, 1H; 8.10, dd, 1H $^{13}$C NMR (CDCl$_3$, δ): 14.74, 20.45, 27.42, 32.66, 35.93, 61.64, 63.57, 112.39, 121.66, 123.29, 124.63, 125.77, 126.54, 126.63, 127.27, 128.89, 141.57, 175.18, 203.04

Step II: Preparation of Perindopril

Method-I

To a suspension of (S,S,S)-Octahydroindole-2-carboxylic acid (1.5 g, 0.0088 moles) in dichloromethane (15 ml) at 25-30° C. was added triethylamine (1.34 ml, 0.0096 moles) and the mixture stirred for 5-10 mns to get a clear solution. The solution was cooled to −10 to −15° C. and to the cooled solution was added N-[1(S)-ethoxycarbonyl butyl]-(S)-alanine-2'-benzothiazolylthiol ester (3.5 g, 0.0106 moles, obtained from Examples 1 and 2), slowly over a period of 1 hr. After the addition was over the temperature was raised to of 25-30° C. and the reaction mixture stirred at this temperature for 15-16 hrs. The reaction mixture was then concentrated under reduced pressure at 30-35° C., to give an oily residue.

The oil was dissolved in a mixture of water (15 ml) and diisopropyl ether (50 ml). The solution was cooled to 0-5° C. and pH of the solution adjusted to 8.3-8.6 using 10% aqueous sodium hydroxide solution. The reaction mixture was stirred at this pH for 15-20 mins, filtered and the organic layer was separated. The aqueous layer was again cooled to 0-5° C. and the pH adjusted to 2.2-2.5 using 6N hydrochloric acid. The aqueous solution was extracted with diisopropyl ether (25 ml×2). The layers were separated and the aqueous layer was cooled to 0-5° C. and the pH adjusted to 3.5-3.8 using 10% aqueous sodium hydroxide solution. Then it was extracted with dichloromethane (50 ml×3). The dichloromethane layer was concentrated under reduced pressure to give: 0.4 g (20%) of Perindopril as a viscous oil.

Method-II

A mixture of (S,S,S)-Octahydroindole-2-carboxylic acid (1.5 g, 0.0088 moles) in acetonitrile (15 ml) was stirred for 5 min. at 25-30° C. To this was added hexamethyl disilazane (1.8 g, 0.011 moles), followed by a few drops of chlorotrimethylsilane. The reaction mixture was heated to reflux for 3-3.5 hrs. When the evolution of ammonia gas evolved during the reaction ceased, the reaction mixture was cooled to 25-30° C. Dichloromethane (20 ml) was added and the mixture was further cooled to 0-5° C. Triethylamine (1.4 ml) was added to the cooled reaction mixture and stirred for 5-10 min and the mixture further cooled to −10 to −20° C. To the cooled reaction mixture was added N-[1(S)-ethoxycarbonyl butyl]-(S)-alanine-2'-benzothiazolylthiol ester (3.5 g, 0.0106 moles, obtained from Examples 1 and 2), slowly over a period of 1 hr. After the addition was over the temperature was raised to 25-30° C. and the mixture stirred at this temperature for 15-16 hrs. The reaction mixture was then concentrated under reduced pressure at 30-35° C. to give an oily residue.

The oil was dissolved in a mixture of water (15 ml) and diisopropyl ether (50 ml). The solution was cooled to 0-5° C. and pH of the solution adjusted to 8.3-8.6 using 10% aqueous sodium hydroxide solution. The reaction mixture was stirred at this pH for 15-20 mins, filtered and the organic layer was separated. The aqueous layer was again cooled to 0-5° C. and the pH adjusted to 2.2-2.5 using 6N hydrochloric acid. The aqueous solution was extracted with diisopropyl ether (25 ml×2). The layers were separated and the aqueous layer was cooled to 0-5° C. and the pH adjusted to 3.5-3.8 using 10% aqueous sodium hydroxide solution. Then it was extracted with dichloromethane (50 ml×3). The dichloromethane layer was concentrated under reduced pressure to give 1.8 g (55%) of Perindopril as a viscous oil.

Method-III

To a suspension of benzyl-(S,S,S)-octahydroindole-2-carboxylate (2.07 g, 0.0079 moles) in dichloromethane (15 ml) at 25-30° C. was added triethylamine (1.34 ml, 0.0096 moles) at the same temperature and the solution obtained was cooled to −10 to −15° C. To the cooled solution was added N-[1(S)-ethoxycarbonyl butyl]-(S)-alanine-2'-benzothiazolylthio ester (3.2 g, 0.0095 moles, obtained in Examples 1 and 2), slowly over a period of 1 hr. After the addition was over the temperature was raised to 25-30° C. and the reaction mixture stirred at this temperature for 8-10 hrs. The reaction mixture was quenched with water (10 ml). The pH of the reaction mixture was adjusted to 8.3-8.6 using 2% aqueous sodium hydroxide solution and stirred at this pH for 15-20 min. The organic layer was separated and washed with water (10 ml). The dichloromethane was concentrated under reduced pressure to give 2.92 g (80%) of Perindopril benzyl ester.

The Perindopril benzyl ester (2.9 g, 6.33 mmoles) dissolved in ethyl alcohol (15 ml) hydrogenated using 10% Palladium on carbon (0.29 g), under 45-50 psi hydrogen pressure for 2.5-3 hrs. The reaction was performed at 25-30° C. After completion of the reaction, the reaction mixture was filtered to remove the catalyst and the filtrate was concentrated under reduced pressure to afford Perindopril as a viscous oil.

REFERENCE EXAMPLE-2

Preparation of Perindopril Erbumine (I) and its Crystallization from Ethyl Acetate as Per the Method Disclosed in U.S. Pat. No. 4,914,214 and Summarized in Scheme-I Perindopril (3 g, 0.0081 moles, as obtained in Reference Example-1) was dissolved in ethyl acetate (42 ml) at 24° C. To the solution was added tertiary butyl amine (0.66 g, 0.009 moles) gradually, under stirring over a period of 15 mns. At the end of the addition, the erbumine salt started separating out. The reaction mixture was heated to reflux till a clear solution resulted. The solution was filtered hot. The filtrate was cooled to 20-25° C. and the solid separated out was collected by filtration. It was dried at 40° C. under reduced pressure for 6 hrs to give 3.38 g (94%) of perindopril erbumine (II), possessing a X-ray (powder) diffraction pattern given in Table-I/FIG. 1 and an IR spectrum given in FIG. 6.

Example 3

Preparation and Crystallization of Perindopril Erbumine (I) from 2,2-dimethoxypropane Obtained from Perindopril as Per the Method Disclosed in U.S. Pat. No. 4,914,214 and Summarized in Scheme-I Perindopril (2 g, 0.0054 moles, as obtained in Reference Example-1) was dissolved in 2,2-dimethoxy propane (36 ml) at 25° C. The solution was filtered over a 0.2μ membrane. To the filtrate was added tertiary butyl amine (0.42 g, 0.0057 moles), gradually under stirring over a period of 12 min. After the addition was over, the salt started separating out in 10 mns. The reaction mixture was then refluxed to obtain a clear solution, filtered hot and the filtrate was allowed to cool gradually to 20-25° C. over 1 hr 25 mns and thereafter, further cooled to 8-12° C. and maintained at this temperature for 30 mns. The crystallized solid product was collected by filtration and dried at 40° C. under reduced pressure for 5 hrs to give 2.2 g (91.7%) of perindopril erbumine (II), possessing the X-ray (powder) diffraction pattern given in Table-IV/FIG. 2 and the IR spectrum given in FIG. 7.

Example 4

Preparation and Crystallization of Perindopril Erbumine (I) from Ethyl Acetate Obtained from Perindopril as Per the Method Disclosed in Our Pending PCT Application No. PCT/IN03/00042, Dated Feb. 28, 2003 and Summarized in Scheme-III Perindopril (4 g, 0.0108 moles, as obtained in Example-1) was dissolved in ethyl acetate (24 ml) at 24° C. To the solution was added tertiary butyl amine (0.88 g, 0.012 moles) gradually under stirring over a period of 15 mns. At the end of the addition, the erbumine salt started separating out. The reaction mixture was heated to reflux till a clear solution resulted. The solution was filtered hot. The filtrate was cooled to 20-25° C. and the product was collected by filtration. It was dried at 40° C. under reduced pressure for 6 hrs to give 4.1 g (85.5%) of perindopril erbumine (II), possessing a X-ray (powder) diffraction pattern given in Table-I/FIG. 1 and an IR spectrum given in FIG. 6.

Example 5

Preparation and Crystallization of Perindopril Erbumine (I) from 2,2-dimethoxypropane Obtained from Perindopril as Per the Method Disclosed in Our Pending PCT Application No. PCT/IN03/00042, Dated Feb. 28, 2003 and Summarized in Scheme-III Perindopril (3 g, 0.0081 moles, as obtained in Example-1) was dissolved in 2,2-dimethoxy propane (57 ml) at 25° C. The solution was filtered over a 0.2μ membrane. To the filtrate was added tertiary butyl amine (0.66 g, 0.009 moles), gradually under stirring over a period of 12 min. After the addition was over, the salt started separating out in 10 mns. The reaction mixture was then refluxed to obtain a clear solution, filtered hot and the filtrate was allowed to cool gradually to 20-25° C. over 1 hr 25 mns and thereafter, further cooled to 8-12° C. and maintained at this temperature for 30 mns. The crystallized solid product was collected by filtration and dried at 40° C. under reduced pressure for 5 hrs to give 3.0 g (83.2%) of perindopril erbumine (II), possessing the X-ray (powder) diffraction pattern given in Table-IV/FIG. 2 and the IR spectrum given in FIG. 7.

Example 6

Preparation and Crystallization of Perindopril Erbumine (I) from Ethyl Acetate Obtained from Perindopril as Per the Method Disclosed in Our Pending PCT Application No. PCT/IN03/00257, Dated Jul. 31, 2003 and Summarized in Scheme-IV Perindopril (4 g, 0.0108 moles, as obtained in Example-2) was dissolved in ethyl acetate (24 ml) at 24° C. To the solution was added tertiary butyl amine (0.66 g, 0.009 moles) gradually under stirring over a period of 15 mins. At the end of the addition, the erbumine salt started separating out. The reaction mixture was heated to reflux till a clear solution resulted. The solution was filtered hot. The filtrate was cooled to 20-25° C. and the product was collected by filtration. It was dried at 40° C. under reduced pressure for 6 hrs to give 4.2 g (87.6%) of perindopril erbumine (II), possessing a X-ray (powder) diffraction pattern given in Table-I/FIG. 1 and an IR spectrum given in FIG. 6.

Example 7

Preparation and Crystallization of Perindopril Erbumine (I) from 2,2-dimethoxypropane Obtained from Perindopril as Per the Method Disclosed in Our Pending PCT Application No. PCT/IN03/00257, Dated Jul. 31, 2003 and Summarized in Scheme-IV Perindopril (3 g, 0.0081 moles, as obtained in Example-2) was dissolved in 2,2-dimethoxy propane (57 ml) at 25° C. The solution was filtered over a 0.2μ membrane. To the filtrate was added tertiary butyl amine (0.66 g, 0.009 moles), gradually under stirring over a period of 12 min. After the addition was over, the salt started separating out in 10 mns. The reaction mixture was then refluxed to obtain a clear solution, filtered hot and the filtrate was allowed to cool gradually to 20-25° C. over 1 hr 25 mns and thereafter, further cooled to 8-12° C. and maintained at this temperature for 30 mns. The crystallized solid product was collected by filtration and dried at 40° C. under reduced pressure for 5 hrs to give 3.1 g (86%) of perindopril erbumine (II), possessing the X-ray (powder) diffraction pattern given in Table-IV/FIG. 2 and the IR spectrum given in FIG. 7.

The invention claimed is:

1. A process for preparation of crystalline perindopril erbumine of formula (II),

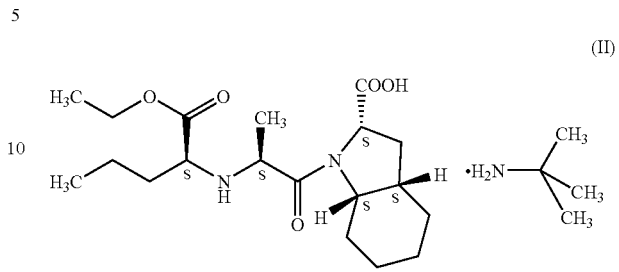

(II)

exhibiting the following X-ray (powder) diffraction pattern,

| d-spacing (Å) | Angle (° 2θ) | Relative Intensity (%) |
|---|---|---|
| 10.239 | 8.628 | 1.16 |
| 8.886 | 9.945 | 49.45 |
| 7.453 | 11.863 | 10.26 |
| 6.054 | 14.618 | 3.35 |
| 5.716 | 15.487 | 14.10 |
| 5.435 | 16.294 | 33.06 |
| 5.082 | 17.434 | 100.00 |
| 4.844 | 18.296 | 14.06 |
| 4.661 | 19.023 | 5.88 |
| 4.278 | 20.744 | 8.50 |
| 4.116 | 21.570 | 17.02 |
| 3.869 | 22.965 | 36.43 |
| 3.565 | 24.950 | 11.58 |
| 3.337 | 26.690 | 6.65 |
| 3.125 | 28.531 | 11.60 |
| 2.993 | 29.823 | 3.93 |
| 2.778 | 32.194 | 4.65 |
| 2.718 | 32.918 | 4.19 |
| 2.619 | 34.196 | 3.28 |
| 2.551 | 35.140 | 2.52 |
| 2.482 | 36.151 | 1.83 |
| 2.391 | 37.578 | 1.77 |
| 2.245 | 40.129 | 0.69 |
| 2.077 | 43.534 | 0.94 | comprising,
reaction of a solution of perindopril of formula (I),

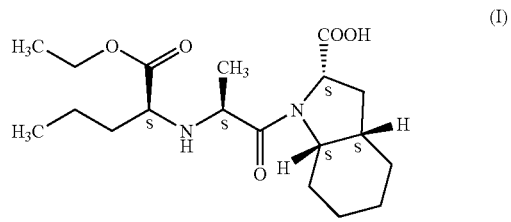

(I)

in a solvent selected from N,N-dimethylformamide, dimethoxymethane, 2,2-dimethoxypropane and 1,2-dimethoxyethane with tertiary butylamine and crystallization of the erbumine salt thus obtained by heating the reaction mixture to reflux, filtering hot, cooling to 20° C. to 30° C., and further cooling to 0° C. to 15° C. for 30 minutes to 1 hour and finally filtering off and drying the crystals.

* * * * *